US006531308B2

(12) United States Patent
Hershberger et al.

(10) Patent No.: US 6,531,308 B2
(45) **Date of Patent: *Mar. 11, 2003**

(54) KETOREDUCTASE GENE AND PROTEIN FROM YEAST

(75) Inventors: Charles Lee Hershberger, Greenfield, IN (US); Robert Allen Payson, Greenwood, IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/415,277

(22) Filed: Oct. 8, 1999

(65) Prior Publication Data

US 2002/0045233 A1 Apr. 18, 2002

Related U.S. Application Data

(63) Continuation-in-part of application No. 09/182,985, filed on Oct. 30, 1998.

(60) Provisional application No. 60/064,195, filed on Nov. 4, 1997.

(51) Int. Cl.[7] ................................................ C12N 15/00

(52) U.S. Cl. ................................ 435/252.3; 435/320.1; 435/252.33; 435/69.1; 435/254.1; 435/254.2; 435/254.21; 536/23.74; 536/23.7; 536/23.2

(58) Field of Search ............................... 536/23.1, 23.2, 536/23.74, 23.7; 435/194, 325, 252.3, 252.33, 254.21, 254.23, 455, 471, 483, 254.2, 69.1

(56) References Cited

U.S. PATENT DOCUMENTS 5,082,767 A 1/1992 Hatfield et al. ................ 435/6

FOREIGN PATENT DOCUMENTS

WO WO 99/29902 6/1999

OTHER PUBLICATIONS

MPSRCH User/Reference Manual, 1994, IntelliGenetics, Inc., Mountain View, CA, pp. 62, 63, and 86–91.*

Dietrich et al, GenBank Accession No. U43834 (Aug. 8, 1997).*

Casamayor et al, Yeast 11: 1281 (1995).*

James et al, Yeast 11: 1413 (1995).*

Hebling et al, GenBank Accession No. Z72561, Entrez Release 24.0, Aug. 15, 1996, National Center for Biotechnology Information, National Institutes of Health, Bethesda, MD.*

Pakula AA & Sauer RT. Genetic analysis of protein stability and function. Annu Rev Genet 1989:23:289–310.*

Grosjean et al., "Preferential Coden Usage in Prokaryotic Genes the Optimal Codon–Anticodon Interaction Energy and the Selective Codon Usage in Efficiently Expressed Genes." Gene 18:199–209 (1982).

Nakamura et al., "Two Types of Linkage Between Codon Usage and Gene–Expression Levels", FEBS LETTERS, 289(1): 123–125, (1991).

Robinson et al., "Codon Usage Can Affect Efficiency of Translation of Genes in *Escherichia Coli*", Nucleic Acids Research, 12(17): 6663–6671, (1984).

Zhang et al., "Low–usage Codons in *Escherichia Coli*, Yeast, Fruit Fly and Primates", Gene, 105 (1): 61–72 (1991).

Zhang et al., "Graphic Analysis of Codon Usage Strategy in 1490 Human Proteins", Journal of Protein Chemistry, 12(3): 329–335, (1993).

Ness, J.E., Welch, M., Giver L., Bueno, M., Cherry, J.R., Borchert, T.V., Stemmer, W.P.C. and Minshull, J., DNA Shuffling of Subgenomic Sequences of Subtilisin, Nat. Biotechnol., 17(9), 893, (1999).

Arnold, F.H. and Moore, J.C., Directed Evolution of Paranitrobenzyl Esterase for Aqueous–Organic Solvents, Nature Biotechnology 14:458–467 (1996).

Stemmer et al., "Rapid Evolution of a Protein In Vitro by DNA Shuffling", Nature 370:389–391 (1994).

Zhao, H., Giver, L., Shao, Z., Affholter, J.A. and Arnold, F.H., Molecular Evolution by Staggered Extension Process (StEP) In Vitro Recombination, Nat. Biotechnol., 16(3), 258, (1998).

* cited by examiner

*Primary Examiner*—James Martinell
(74) *Attorney, Agent, or Firm*—Paula K. Davis; Thomas D. Webster

(57) ABSTRACT

The invention provides cloned ketoreductase genes, vectors for expressing same, recombinant host cells that express said vector-borne genes, a method for stereospecifically reducing a ketone using a recombinant ketoreductase, or a recombinant host cell that expresses a cloned ketoreductase gene, as well as a method for generating polynucleotide sequences more conducive to recombinant expression.

6 Claims, No Drawings

SEQUENCE LISTING

```
<160> NUMBER OF SEQ ID NOS:  17

<210> SEQ ID NO 1
<211> LENGTH: 1270
<212> TYPE: DNA
<213> ORGANISM: z. rouxii
<220> FEATURE:
<221> NAME/KEY: CDS
<222> LOCATION: (164)..(1177)

<400> SEQUENCE: 1

tgaatggtta ttttagcaat tgctgtgtga ggcactgacc taaagatgtg tataaatagt     60

gggactgtgt actcatgagg atcaatacat gtataaactt accatacttt cacacaagtc    120

aacttagaat caatcaatca atcaattaat caagctatac aat atg aca aaa gtc      175
                                                Met Thr Lys Val
                                                  1

ttc gta aca ggt gcc aac gga ttc gtt gct caa cac gtc gtt cat caa      223
Phe Val Thr Gly Ala Asn Gly Phe Val Ala Gln His Val Val His Gln
  5                  10                  15                  20

cta tta gaa aag aac tat aca gtg gtt gga tct gtc cgt tca act gag      271
Leu Leu Glu Lys Asn Tyr Thr Val Val Gly Ser Val Arg Ser Thr Glu
                 25                  30                  35

aaa ggt gat aaa tta gct aaa ttg cta aac aat cca aaa ttt tca tat      319
Lys Gly Asp Lys Leu Ala Lys Leu Leu Asn Asn Pro Lys Phe Ser Tyr
             40                  45                  50

gag att att aaa gat atg gtc aat tcg aga gat gaa ttc gat aag gct      367
Glu Ile Ile Lys Asp Met Val Asn Ser Arg Asp Glu Phe Asp Lys Ala
         55                  60                  65

tta caa aaa cat tca gat gtt gaa att gtc tta cat act gct tca cca      415
Leu Gln Lys His Ser Asp Val Glu Ile Val Leu His Thr Ala Ser Pro
     70                  75                  80

gtc ttc cca ggt ggt att aaa gat gtt gaa aaa gaa atg atc caa cca      463
Val Phe Pro Gly Gly Ile Lys Asp Val Glu Lys Glu Met Ile Gln Pro
 85                  90                  95                 100

gct gtt aat ggt act aga aat gtc ttg tta tca atc aag gat aac tta      511
Ala Val Asn Gly Thr Arg Asn Val Leu Leu Ser Ile Lys Asp Asn Leu
                105                 110                 115

cca aat gtc aag aga ttt gtt tac act tct tca tta gct gct gtc cgt      559
Pro Asn Val Lys Arg Phe Val Tyr Thr Ser Ser Leu Ala Ala Val Arg
            120                 125                 130

act gaa ggt gct ggt tat agt gca gac gaa gtt gtc acc gaa gat tct      607
Thr Glu Gly Ala Gly Tyr Ser Ala Asp Glu Val Val Thr Glu Asp Ser
        135                 140                 145

tgg aac aat att gca ttg aaa gat gcc acc aag gat gaa ggt aca gct      655
Trp Asn Asn Ile Ala Leu Lys Asp Ala Thr Lys Asp Glu Gly Thr Ala
    150                 155                 160

tat gag gct tcc aag aca tat ggt gaa aaa gaa gtt tgg aat ttc ttc      703
Tyr Glu Ala Ser Lys Thr Tyr Gly Glu Lys Glu Val Trp Asn Phe Phe
165                 170                 175                 180

gaa aaa act aaa aat gtt aat ttc gat ttt gcc atc atc aac cca gtt      751
Glu Lys Thr Lys Asn Val Asn Phe Asp Phe Ala Ile Ile Asn Pro Val
                185                 190                 195

tat gtc ttt ggt cct caa tta ttt gaa gaa tac gtt act gat aaa ttg      799
Tyr Val Phe Gly Pro Gln Leu Phe Glu Glu Tyr Val Thr Asp Lys Leu
            200                 205                 210

aac ttt tcc agt gaa atc att aat agt ata ata aaa ggt gaa aag aag      847
Asn Phe Ser Ser Glu Ile Ile Asn Ser Ile Ile Lys Gly Glu Lys Lys
        215                 220                 225
```

-continued

```
gaa att gaa ggt tat gaa att gat gtt aga gat att gca aga gct cat      895
Glu Ile Glu Gly Tyr Glu Ile Asp Val Arg Asp Ile Ala Arg Ala His
    230                 235                 240

atc tct gct gtt gaa aat cca gca act aca cgt caa aga tta att cca      943
Ile Ser Ala Val Glu Asn Pro Ala Thr Thr Arg Gln Arg Leu Ile Pro
245                 250                 255                 260

gca gtt gca cca tac aat caa caa act atc ttg gat gtt ttg aat gaa      991
Ala Val Ala Pro Tyr Asn Gln Gln Thr Ile Leu Asp Val Leu Asn Glu
                265                 270                 275

aac ttc cca gaa ttg aaa ggt aaa atc gat gtt ggg aaa cca ggt tct     1039
Asn Phe Pro Glu Leu Lys Gly Lys Ile Asp Val Gly Lys Pro Gly Ser
            280                 285                 290

caa aat gaa ttt att aaa aaa tat tat aaa tta gat aac tca aag acc     1087
Gln Asn Glu Phe Ile Lys Lys Tyr Tyr Lys Leu Asp Asn Ser Lys Thr
        295                 300                 305

aaa aaa gtt tta ggt ttt gaa ttc att tcc caa gag caa aca atc aaa     1135
Lys Lys Val Leu Gly Phe Glu Phe Ile Ser Gln Glu Gln Thr Ile Lys
    310                 315                 320

gat gct gct gct caa atc ttg tcc gtt aaa aat gga aaa aaa             1177
Asp Ala Ala Ala Gln Ile Leu Ser Val Lys Asn Gly Lys Lys
325                 330                 335

taagtgaact agacctgtca ctatcagatt attagagttc tgtatagatt aaagtgtgaa   1237

aatgtattag aatcataatt ttataatatg cct                                1270


<210> SEQ ID NO 2
<211> LENGTH: 338
<212> TYPE: PRT
<213> ORGANISM: z. rouxii

<400> SEQUENCE: 2

Met Thr Lys Val Phe Val Thr Gly Ala Asn Gly Phe Val Ala Gln His
  1               5                  10                  15

Val Val His Gln Leu Leu Glu Lys Asn Tyr Thr Val Val Gly Ser Val
            20                  25                  30

Arg Ser Thr Glu Lys Gly Asp Lys Leu Ala Lys Leu Leu Asn Asn Pro
        35                  40                  45

Lys Phe Ser Tyr Glu Ile Ile Lys Asp Met Val Asn Ser Arg Asp Glu
     50                  55                  60

Phe Asp Lys Ala Leu Gln Lys His Ser Asp Val Glu Ile Val Leu His
 65                  70                  75                  80

Thr Ala Ser Pro Val Phe Pro Gly Gly Ile Lys Asp Val Glu Lys Glu
                 85                  90                  95

Met Ile Gln Pro Ala Val Asn Gly Thr Arg Asn Val Leu Leu Ser Ile
            100                 105                 110

Lys Asp Asn Leu Pro Asn Val Lys Arg Phe Val Tyr Thr Ser Ser Leu
        115                 120                 125

Ala Ala Val Arg Thr Glu Gly Ala Gly Tyr Ser Ala Asp Glu Val Val
    130                 135                 140

Thr Glu Asp Ser Trp Asn Asn Ile Ala Leu Lys Asp Ala Thr Lys Asp
145                 150                 155                 160

Glu Gly Thr Ala Tyr Glu Ala Ser Lys Thr Tyr Gly Glu Lys Glu Val
                165                 170                 175

Trp Asn Phe Phe Glu Lys Thr Lys Asn Val Asn Phe Asp Phe Ala Ile
            180                 185                 190

Ile Asn Pro Val Tyr Val Phe Gly Pro Gln Leu Phe Glu Glu Tyr Val
        195                 200                 205
```

-continued

```
Thr Asp Lys Leu Asn Phe Ser Ser Glu Ile Ile Asn Ser Ile Ile Lys
    210                 215                 220

Gly Glu Lys Lys Glu Ile Glu Gly Tyr Glu Ile Asp Val Arg Asp Ile
225                 230                 235                 240

Ala Arg Ala His Ile Ser Ala Val Glu Asn Pro Ala Thr Thr Arg Gln
                245                 250                 255

Arg Leu Ile Pro Ala Val Ala Pro Tyr Asn Gln Gln Thr Ile Leu Asp
            260                 265                 270

Val Leu Asn Glu Asn Phe Pro Glu Leu Lys Gly Lys Ile Asp Val Gly
        275                 280                 285

Lys Pro Gly Ser Gln Asn Glu Phe Ile Lys Lys Tyr Tyr Lys Leu Asp
    290                 295                 300

Asn Ser Lys Thr Lys Lys Val Leu Gly Phe Glu Phe Ile Ser Gln Glu
305                 310                 315                 320

Gln Thr Ile Lys Asp Ala Ala Ala Gln Ile Leu Ser Val Lys Asn Gly
                325                 330                 335

Lys Lys


<210> SEQ ID NO 3
<211> LENGTH: 1271
<212> TYPE: RNA
<213> ORGANISM: z. rouxii

<400> SEQUENCE: 3

ugaaugguua uuuuagcaau ugcuguguga ggcacugacc uaaagaugug uauaaaauagu      60

gggacugugu acucaugagg aucaauacau guauaaacuu accauacuuu cacacaaguc     120

aacuuagaau caaucaauca aucaauuaau caagcuauac aauaugacaa aagucuucgu     180

aacaggugcc aacggauucg uugcucaaca cgucguucau caacuauuag aaaagaacua     240

uacagugguu ggaucugucc guucaacuga gaaaggugau aaauuagcua aauugcuaaa     300

caauccaaaa uuuucauaug agauuauuaa agauauggue aauucgagag augaauucga     360

uaaggcuuua caaaaacauu cagauguuga aauugucuua cauacugcuu caccagucuu     420

cccaggugu auuaaagaug uugaaaaaga aaugauccaa ccagcuguua augguacuag     480

aaaugucuug uuaucaauca aggauaacuu accaaauguc aagagauuug uuuacacuuc     540

uucauuagcu gcuguccgua cugaaggugc ugguuauagu gcagacgaag uugucaccga     600

agauucuugg aacaauauug cauugaaaga ugccaccaag gaugaaggua cagcuuauga     660

ggcuuccaag acauauggug aaaaagaagu uuggaauuuc uucgaaaaaa cuaaaaaugu     720

uaauuucgau uuugccauca ucaacccagu uuaugucuuu gguccucaau uauuugaaga     780

auacguuacu gauaaauuga acuuuuccag ugaaaucauu aauaguauaa uaaaagguga     840

aaagaaggaa auugaagguu augaaauuga uguuagagau auugcaagag cucauaucuc     900

ugcuguugaa aauccagcaa cuacacguca aagauuaauu ccagcaguug caccauacaa     960

ucaacaaacu aucuuggaug uuuugaauga aaacuuccca gaauugaaag guaaaaucga    1020

uguugggaaa ccagguucuc aaaaugaauu uauuaaaaaa uauuauaaau uagauaacuc    1080

aaagaccaaa aaaguuuuag guuuugaauu cauuucccaa gagcaaacaa ucaaagaugc    1140

ugcugcucaa aucuuguccg uuaaaaaugg aaaaaaauaa gugaacuaga ccugucacua    1200

ucagauuauu agaguucugu auagauuaaa gugugaaaau guauuagaau cauaauuuua    1260

uaauuaugcc u                                                          1271
```

```
<210> SEQ ID NO 4
<211> LENGTH: 1032
<212> TYPE: DNA
<213> ORGANISM: s. cerevisiae
<220> FEATURE:
<221> NAME/KEY: CDS
<222> LOCATION: (1)..(1032)

<400> SEQUENCE: 4

atg tct aat aca gtt cta gtt tct ggc gct tca ggt ttt att gcc ttg   48
Met Ser Asn Thr Val Leu Val Ser Gly Ala Ser Gly Phe Ile Ala Leu
  1               5                  10                  15

cat atc ctg tca caa ttg tta aaa caa gat tat aag gtt att gga act   96
His Ile Leu Ser Gln Leu Leu Lys Gln Asp Tyr Lys Val Ile Gly Thr
             20                  25                  30

gtg aga tcc cat gaa aaa gaa gca aaa ttg cta aga caa ttt caa cat  144
Val Arg Ser His Glu Lys Glu Ala Lys Leu Leu Arg Gln Phe Gln His
         35                  40                  45

aac cct aat tta act tta gaa att gtt ccg gac att tct cat cca aat  192
Asn Pro Asn Leu Thr Leu Glu Ile Val Pro Asp Ile Ser His Pro Asn
     50                  55                  60

gct ttc gat aag gtt ctg cag aaa cgt gga cgt gag att agg tat gtt  240
Ala Phe Asp Lys Val Leu Gln Lys Arg Gly Arg Glu Ile Arg Tyr Val
 65                  70                  75                  80

cta cac acg gcc tct cct ttt cat tat gat act acc gaa tat gaa aaa  288
Leu His Thr Ala Ser Pro Phe His Tyr Asp Thr Thr Glu Tyr Glu Lys
                 85                  90                  95

gac tta ttg att ccc gcg tta gaa ggt aca aaa aac atc cta aat tct  336
Asp Leu Leu Ile Pro Ala Leu Glu Gly Thr Lys Asn Ile Leu Asn Ser
            100                 105                 110

atc aag aaa tat gca gca gac act gta gag cgt gtt gtt gtg act tct  384
Ile Lys Lys Tyr Ala Ala Asp Thr Val Glu Arg Val Val Val Thr Ser
        115                 120                 125

tct tgt act gct att ata acc ctt gca aag atg gac gat ccc agt gtg  432
Ser Cys Thr Ala Ile Ile Thr Leu Ala Lys Met Asp Asp Pro Ser Val
    130                 135                 140

gtt ttt aca gaa gag agt tgg aac gaa gca acc tgg gaa agc tgt caa  480
Val Phe Thr Glu Glu Ser Trp Asn Glu Ala Thr Trp Glu Ser Cys Gln
145                 150                 155                 160

att gat ggg ata aat gct tac ttt gca tcc aag aag ttt gct gaa aag  528
Ile Asp Gly Ile Asn Ala Tyr Phe Ala Ser Lys Lys Phe Ala Glu Lys
                165                 170                 175

gct gcc tgg gag ttc aca aaa gag aat gaa gat cac atc aaa ttc aaa  576
Ala Ala Trp Glu Phe Thr Lys Glu Asn Glu Asp His Ile Lys Phe Lys
            180                 185                 190

cta aca aca gtc aac cct tct ctt ctt ttt ggt cct caa ctt ttc gat  624
Leu Thr Thr Val Asn Pro Ser Leu Leu Phe Gly Pro Gln Leu Phe Asp
        195                 200                 205

gaa gat gtg cat ggc cat ttg aat act tct tgc gaa atg atc aat ggc  672
Glu Asp Val His Gly His Leu Asn Thr Ser Cys Glu Met Ile Asn Gly
    210                 215                 220

cta att cat acc cca gta aat gcc agt gtt cct gat ttt cat tcc att  720
Leu Ile His Thr Pro Val Asn Ala Ser Val Pro Asp Phe His Ser Ile
225                 230                 235                 240

ttt att gat gta agg gat gtg gcc cta gct cat ctg tat gct ttc cag  768
Phe Ile Asp Val Arg Asp Val Ala Leu Ala His Leu Tyr Ala Phe Gln
                245                 250                 255

aag gaa aat acc gcg ggt aaa aga tta gtg gta act aac ggt aaa ttt  816
Lys Glu Asn Thr Ala Gly Lys Arg Leu Val Val Thr Asn Gly Lys Phe
            260                 265                 270

gga aac caa gat atc ctg gat att ttg aac gaa gat ttt cca caa tta  864
```

-continued

```
Gly Asn Gln Asp Ile Leu Asp Ile Leu Asn Glu Asp Phe Pro Gln Leu
        275                 280                 285

aga ggt ctc att cct ttg ggt aag cct ggc aca ggt gat caa gtc att    912
Arg Gly Leu Ile Pro Leu Gly Lys Pro Gly Thr Gly Asp Gln Val Ile
    290                 295                 300

gac cgc ggt tca act aca gat aat agt gca acg agg aaa ata ctt ggc    960
Asp Arg Gly Ser Thr Thr Asp Asn Ser Ala Thr Arg Lys Ile Leu Gly
305                 310                 315                 320

ttt gag ttc aga agt tta cac gaa agt gtc cat gat act gct gcc caa   1008
Phe Glu Phe Arg Ser Leu His Glu Ser Val His Asp Thr Ala Ala Gln
                325                 330                 335

att ttg aag aag gag aac aga tta                                   1032
Ile Leu Lys Lys Glu Asn Arg Leu
            340


<210> SEQ ID NO 5
<211> LENGTH: 344
<212> TYPE: PRT
<213> ORGANISM: s. cerevisiae

<400> SEQUENCE: 5

Met Ser Asn Thr Val Leu Val Ser Gly Ala Ser Gly Phe Ile Ala Leu
  1               5                  10                  15

His Ile Leu Ser Gln Leu Leu Lys Gln Asp Tyr Lys Val Ile Gly Thr
            20                  25                  30

Val Arg Ser His Glu Lys Glu Ala Lys Leu Leu Arg Gln Phe Gln His
        35                  40                  45

Asn Pro Asn Leu Thr Leu Glu Ile Val Pro Asp Ile Ser His Pro Asn
    50                  55                  60

Ala Phe Asp Lys Val Leu Gln Lys Arg Gly Arg Glu Ile Arg Tyr Val
65                  70                  75                  80

Leu His Thr Ala Ser Pro Phe His Tyr Asp Thr Thr Glu Tyr Glu Lys
                85                  90                  95

Asp Leu Leu Ile Pro Ala Leu Glu Gly Thr Lys Asn Ile Leu Asn Ser
            100                 105                 110

Ile Lys Lys Tyr Ala Ala Asp Thr Val Glu Arg Val Val Val Thr Ser
        115                 120                 125

Ser Cys Thr Ala Ile Ile Thr Leu Ala Lys Met Asp Asp Pro Ser Val
    130                 135                 140

Val Phe Thr Glu Glu Ser Trp Asn Glu Ala Thr Trp Glu Ser Cys Gln
145                 150                 155                 160

Ile Asp Gly Ile Asn Ala Tyr Phe Ala Ser Lys Lys Phe Ala Glu Lys
                165                 170                 175

Ala Ala Trp Glu Phe Thr Lys Glu Asn Glu Asp His Ile Lys Phe Lys
            180                 185                 190

Leu Thr Thr Val Asn Pro Ser Leu Leu Phe Gly Pro Gln Leu Phe Asp
        195                 200                 205

Glu Asp Val His Gly His Leu Asn Thr Ser Cys Glu Met Ile Asn Gly
    210                 215                 220

Leu Ile His Thr Pro Val Asn Ala Ser Val Pro Asp Phe His Ser Ile
225                 230                 235                 240

Phe Ile Asp Val Arg Asp Val Ala Leu Ala His Leu Tyr Ala Phe Gln
                245                 250                 255

Lys Glu Asn Thr Ala Gly Lys Arg Leu Val Val Thr Asn Gly Lys Phe
            260                 265                 270

Gly Asn Gln Asp Ile Leu Asp Ile Leu Asn Glu Asp Phe Pro Gln Leu
```

-continued

```
        275                 280                 285

Arg Gly Leu Ile Pro Leu Gly Lys Pro Gly Thr Gly Asp Gln Val Ile
    290                 295                 300

Asp Arg Gly Ser Thr Thr Asp Asn Ser Ala Thr Arg Lys Ile Leu Gly
305                 310                 315                 320

Phe Glu Phe Arg Ser Leu His Glu Ser Val His Asp Thr Ala Ala Gln
                325                 330                 335

Ile Leu Lys Lys Glu Asn Arg Leu
            340


<210> SEQ ID NO 6
<211> LENGTH: 1032
<212> TYPE: RNA
<213> ORGANISM: s. cerevisiae

<400> SEQUENCE: 6

augucuaaua caguucuagu uucuggcgcu ucagguuuua uugccuugca uauccuguca     60

caauuguuaa aacaagauua uaagguuauu ggaacuguga gaucccauga aaaagaagca    120

aaauugcuaa gacaauuuca acauaacccu aauuuaacuu uagaaauugu uccggacauu    180

ucucauccaa augcuuucga uaagguucug cagaaacgug gacgugagau uagguauguu    240

cuacacacgg ccucucccuu ucauuaugau acuaccgaau augaaaaaga cuuauugauu    300

cccgcguuag aagguacaaa aaacauccua aauucuauca agaaauaugc agcagacacu    360

guagagcgug uuguugugac uucuucuugu acugcuauua uaacccuugc aaagauggac    420

gaucccagug ugguuuuuac agaagagagu uggaacgaag caaccuggga aagcugucaa    480

auugauggga uaaaugcuua cuuugcaucc aagaaguuug cugaaaaggc ugccugggag    540

uucacaaaag agaaugaaga ucacaucaaa uucaaacuaa caacagucaa cccuucucuu    600

cuuuuugguc cucaacuuuu cgaugaagau gugcauggcc auuugaauac uucuugcgaa    660

augaucaaug gccuaauuca uaccccagua aaugccagug uuccugauuu ucauuccauu    720

uuuauugaug uaagggaugu ggcccuagcu caucuguaug cuuuccagaa ggaaaauacc    780

gcggguaaaa gauuaguggu aacuaacggu aaauuuggaa accaagauau ccuggauauu    840

uugaacgaag auuuuccaca auuaagaggu cucauuccuu ugggaagcc uggcacaggu    900

gaucaaguca uugaccgcgg uucaacuaca gauaauagug caacgaggaa aauacuuggc    960

uuugaguuca gaaguuuaca cgaaagugug caugauacug cugcccaaau uuugaagaag   1020

gagaacagau ua                                                        1032


<210> SEQ ID NO 7
<211> LENGTH: 1029
<212> TYPE: DNA
<213> ORGANISM: s. cerevisiae
<220> FEATURE:
<221> NAME/KEY: CDS
<222> LOCATION: (1)..(1026)

<400> SEQUENCE: 7

atg tca gtt ttc gtt tca ggt gct aac ggg ttc att gcc caa cac att   48
Met Ser Val Phe Val Ser Gly Ala Asn Gly Phe Ile Ala Gln His Ile
  1               5                  10                  15

gtc gat ctc ctg ttg aag gaa gac tat aag gtc atc ggt tct gcc aga   96
Val Asp Leu Leu Leu Lys Glu Asp Tyr Lys Val Ile Gly Ser Ala Arg
             20                  25                  30

agt caa gaa aag gcc gag aat tta acg gag gcc ttt ggt aac aac cca   144
Ser Gln Glu Lys Ala Glu Asn Leu Thr Glu Ala Phe Gly Asn Asn Pro
```

-continued

```
        35                  40                  45

aaa ttc tcc atg gaa gtt gtc cca gac ata tct aag ctg gac gca ttt   192
Lys Phe Ser Met Glu Val Val Pro Asp Ile Ser Lys Leu Asp Ala Phe
     50                  55                  60

gac cat gtt ttc caa aag cac ggc aag gat atc aag ata gtt cta cat   240
Asp His Val Phe Gln Lys His Gly Lys Asp Ile Lys Ile Val Leu His
 65                  70                  75                  80

acg gcc tct cca ttc tgc ttt gat atc act gac agt gaa cgc gat tta   288
Thr Ala Ser Pro Phe Cys Phe Asp Ile Thr Asp Ser Glu Arg Asp Leu
                 85                  90                  95

tta att cct gct gtg aac ggt gtt aag gga att ctc cac tca att aaa   336
Leu Ile Pro Ala Val Asn Gly Val Lys Gly Ile Leu His Ser Ile Lys
            100                 105                 110

aaa tac gcc gct gat tct gta gaa cgt gta gtt ctc acc tct tct tat   384
Lys Tyr Ala Ala Asp Ser Val Glu Arg Val Val Leu Thr Ser Ser Tyr
        115                 120                 125

gca gct gtg ttc gat atg gca aaa gaa aac gat aag tct tta aca ttt   432
Ala Ala Val Phe Asp Met Ala Lys Glu Asn Asp Lys Ser Leu Thr Phe
    130                 135                 140

aac gaa gaa tcc tgg aac cca gct acc tgg gag agt tgc caa agt gac   480
Asn Glu Glu Ser Trp Asn Pro Ala Thr Trp Glu Ser Cys Gln Ser Asp
145                 150                 155                 160

cca gtt aac gcc tac tgt ggt tct aag aag ttt gct gaa aaa gca gct   528
Pro Val Asn Ala Tyr Cys Gly Ser Lys Lys Phe Ala Glu Lys Ala Ala
                165                 170                 175

tgg gaa ttt cta gag gag aat aga gac tct gta aaa ttc gaa tta act   576
Trp Glu Phe Leu Glu Glu Asn Arg Asp Ser Val Lys Phe Glu Leu Thr
            180                 185                 190

gcc gtt aac cca gtt tac gtt ttt ggt ccg caa atg ttt gac aaa gat   624
Ala Val Asn Pro Val Tyr Val Phe Gly Pro Gln Met Phe Asp Lys Asp
        195                 200                 205

gtg aaa aaa cac ttg aac aca tct tgc gaa ctc gtc aac agc ttg atg   672
Val Lys Lys His Leu Asn Thr Ser Cys Glu Leu Val Asn Ser Leu Met
    210                 215                 220

cat tta tca cca gag gac aag ata ccg gaa cta ttt ggt gga tac att   720
His Leu Ser Pro Glu Asp Lys Ile Pro Glu Leu Phe Gly Gly Tyr Ile
225                 230                 235                 240

gat gtt cgt gat gtt gca aag gct cat tta gtt gcc ttc caa aag agg   768
Asp Val Arg Asp Val Ala Lys Ala His Leu Val Ala Phe Gln Lys Arg
                245                 250                 255

gaa aca att ggt caa aga cta atc gta tcg gag gcc aga ttt act atg   816
Glu Thr Ile Gly Gln Arg Leu Ile Val Ser Glu Ala Arg Phe Thr Met
            260                 265                 270

cag gat gtt ctc gat atc ctt aac gaa gac ttc cct gtt cta aaa ggc   864
Gln Asp Val Leu Asp Ile Leu Asn Glu Asp Phe Pro Val Leu Lys Gly
        275                 280                 285

aat att cca gtg ggg aaa cca ggt tct ggt gct acc cat aac acc ctt   912
Asn Ile Pro Val Gly Lys Pro Gly Ser Gly Ala Thr His Asn Thr Leu
    290                 295                 300

ggt gct act ctt gat aat aaa aag agt aag aaa ttg tta ggt ttc aag   960
Gly Ala Thr Leu Asp Asn Lys Lys Ser Lys Lys Leu Leu Gly Phe Lys
305                 310                 315                 320

ttc agg aac ttg aaa gag acc att gac gac act gcc tcc caa att tta  1008
Phe Arg Asn Leu Lys Glu Thr Ile Asp Asp Thr Ala Ser Gln Ile Leu
                325                 330                 335

aaa ttt gag ggc aga ata taa                                      1029
Lys Phe Glu Gly Arg Ile
            340
```

-continued

```
<210> SEQ ID NO 8
<211> LENGTH: 342
<212> TYPE: PRT
<213> ORGANISM: s. cerevisiae

<400> SEQUENCE: 8

Met Ser Val Phe Val Ser Gly Ala Asn Gly Phe Ile Ala Gln His Ile
  1               5                  10                  15

Val Asp Leu Leu Leu Lys Glu Asp Tyr Lys Val Ile Gly Ser Ala Arg
             20                  25                  30

Ser Gln Glu Lys Ala Glu Asn Leu Thr Glu Ala Phe Gly Asn Asn Pro
         35                  40                  45

Lys Phe Ser Met Glu Val Val Pro Asp Ile Ser Lys Leu Asp Ala Phe
     50                  55                  60

Asp His Val Phe Gln Lys His Gly Lys Asp Ile Lys Ile Val Leu His
 65                  70                  75                  80

Thr Ala Ser Pro Phe Cys Phe Asp Ile Thr Asp Ser Glu Arg Asp Leu
                 85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340


<210> SEQ ID NO 9
<211> LENGTH: 1026
<212> TYPE: RNA
<213> ORGANISM: s. cerevisiae
```

-continued

<400> SEQUENCE: 9

```
augucaguuu ucguuucagg ugcuaacggg uucauugccc aacacauugu cgaucuccug     60
uugaaggaag acuauaaggu caucgguucu gccagaaguc aagaaaaggc cgagaauuua    120
acggaggccu uugguaacaa cccaaaauuc uccauggaag uugucccaga cauaucuaag    180
cuggacgcau uugaccaugu uuuccaaaag cacggcaagg auaucaagau aguucuacau    240
acggccucuc cauucugcuu ugauaucacu gacagugaac gcgauuuauu aauuccugcu    300
gugaacggug uuaagggaau ucuccacuca auuaaaaaau acgccgcuga uucuguagaa    360
cguguaguuc ucaccucuuc uuaugcagcu guguucgaua uggcaaaaga aaacgauaag    420
ucuuuaacau uuaacgaaga auccuggaac ccagcuaccu gggagaguug ccaaagugac    480
ccaguuaacg ccuacugugg uucuaagaag uuugcugaaa aagcagcuug ggaauuucua    540
gaggagaaua gagacucugu aaaauucgaa uuaacugccg uuaacccagu uuacguuuuu    600
gguccgcaaa uguuugacaa agaugugaaa aaacacuuga acacaucuug cgaacucguc    660
aacagcuuga ugcauuuauc accagaggac aagauaccgg aacuauuugg uggauacauu    720
gauguucgug auguugcaaa ggcucauuua guugccuucc aaaagaggga aacaauuggu    780
caaagacuaa ucguaucgga ggccagauuu acuaugcagg auguucucga uauccuuaac    840
gaagacuucc cuguucuaaa aggcaauauu ccagugggga aaccagguuc uggugcuacc    900
cauaacaccc uuggugcuac ucuugauaau aaaaagagua agaaauuguu agguuucaag    960
uucaggaacu ugaaagagac cauugacgac acugccuccc aaauuuuaaa auuugagggc   1020
agaaua                                                              1026
```

<210> SEQ ID NO 10
<211> LENGTH: 1041
<212> TYPE: DNA
<213> ORGANISM: s. cerevisiae
<220> FEATURE:
<221> NAME/KEY: CDS
<222> LOCATION: (1)..(1041)

<400> SEQUENCE: 10

```
atg act act gat acc act gtt ttc gtt tct ggc gca acc ggt ttc att   48
Met Thr Thr Asp Thr Thr Val Phe Val Ser Gly Ala Thr Gly Phe Ile
  1               5                  10                  15

gct cta cac att atg aac gat ctg ttg aaa gct ggc tat aca gtc atc   96
Ala Leu His Ile Met Asn Asp Leu Leu Lys Ala Gly Tyr Thr Val Ile
             20                  25                  30

ggc tca ggt aga tct caa gaa aaa aat gat ggc ttg ctc aaa aaa ttt   144
Gly Ser Gly Arg Ser Gln Glu Lys Asn Asp Gly Leu Leu Lys Lys Phe
         35                  40                  45

aat aac aat ccc aaa cta tcg atg gaa att gtg gaa gat att gct gct   192
Asn Asn Asn Pro Lys Leu Ser Met Glu Ile Val Glu Asp Ile Ala Ala
     50                  55                  60

cca aac gcc ttt gat gaa gtt ttc aaa aaa cat ggt aag gaa att aag   240
Pro Asn Ala Phe Asp Glu Val Phe Lys Lys His Gly Lys Glu Ile Lys
 65                  70                  75                  80

att gtg cta cac act gcc tcc cca ttc cat ttt gaa act acc aat ttt   288
Ile Val Leu His Thr Ala Ser Pro Phe His Phe Glu Thr Thr Asn Phe
                 85                  90                  95

gaa aag gat tta cta acc cct gca gtg aac ggt aca aaa tct atc ttg   336
Glu Lys Asp Leu Leu Thr Pro Ala Val Asn Gly Thr Lys Ser Ile Leu
            100                 105                 110

gaa gcg att aaa aaa tat gct gca gac act gtt gaa aaa gtt att gtt   384
Glu Ala Ile Lys Lys Tyr Ala Ala Asp Thr Val Glu Lys Val Ile Val
```

-continued

```
        115                 120                 125

act tcg tct act gct gct ctg gtg aca cct aca gac atg aac aaa gga    432
Thr Ser Ser Thr Ala Ala Leu Val Thr Pro Thr Asp Met Asn Lys Gly
    130                 135                 140

gat ttg gtg atc acg gag gag agt tgg aat aag gat aca tgg gac agt    480
Asp Leu Val Ile Thr Glu Glu Ser Trp Asn Lys Asp Thr Trp Asp Ser
145                 150                 155                 160

tgt caa gcc aac gcc gtt gcc gca tat tgt ggc tcg aaa aag ttt gct    528
Cys Gln Ala Asn Ala Val Ala Ala Tyr Cys Gly Ser Lys Lys Phe Ala
                165                 170                 175

gaa aaa act gct tgg gaa ttt ctt aaa gaa aac aag tct agt gtc aaa    576
Glu Lys Thr Ala Trp Glu Phe Leu Lys Glu Asn Lys Ser Ser Val Lys
            180                 185                 190

ttc aca cta tcc act atc aat ccg gga ttc gtt ttt ggt cct caa atg    624
Phe Thr Leu Ser Thr Ile Asn Pro Gly Phe Val Phe Gly Pro Gln Met
        195                 200                 205

ttt gca gat tcg cta aaa cat ggc ata aat acc tcc tca ggg atc gta    672
Phe Ala Asp Ser Leu Lys His Gly Ile Asn Thr Ser Ser Gly Ile Val
    210                 215                 220

tct gag tta att cat tcc aag gta ggt gga gaa ttt tat aat tac tgt    720
Ser Glu Leu Ile His Ser Lys Val Gly Gly Glu Phe Tyr Asn Tyr Cys
225                 230                 235                 240

ggc cca ttt att gac gtg cgt gac gtt tct aaa gcc cac cta gtt gca    768
Gly Pro Phe Ile Asp Val Arg Asp Val Ser Lys Ala His Leu Val Ala
                245                 250                 255

att gaa aaa cca gaa tgt acc ggc caa aga tta gta ttg agt gaa ggt    816
Ile Glu Lys Pro Glu Cys Thr Gly Gln Arg Leu Val Leu Ser Glu Gly
            260                 265                 270

tta ttc tgc tgt caa gaa atc gtt gac atc ttg aac gag gaa ttc cct    864
Leu Phe Cys Cys Gln Glu Ile Val Asp Ile Leu Asn Glu Glu Phe Pro
        275                 280                 285

caa tta aag ggc aag ata gct aca ggt gaa cct gcg acc ggt cca agc    912
Gln Leu Lys Gly Lys Ile Ala Thr Gly Glu Pro Ala Thr Gly Pro Ser
    290                 295                 300

ttt tta gaa aaa aac tct tgc aag ttt gac aat tct aag aca aaa aaa    960
Phe Leu Glu Lys Asn Ser Cys Lys Phe Asp Asn Ser Lys Thr Lys Lys
305                 310                 315                 320

cta ctg gga ttc cag ttt tac aat tta aag gat tgc ata gtt gac acc    1008
Leu Leu Gly Phe Gln Phe Tyr Asn Leu Lys Asp Cys Ile Val Asp Thr
                325                 330                 335

gcg gcg caa atg tta gaa gtt caa aat gaa gcc                        1041
Ala Ala Gln Met Leu Glu Val Gln Asn Glu Ala
            340                 345


<210> SEQ ID NO 11
<211> LENGTH: 347
<212> TYPE: PRT
<213> ORGANISM: s. cerevisiae

<400> SEQUENCE: 11

Met Thr Thr Asp Thr Thr Val Phe Val Ser Gly Ala Thr Gly Phe Ile
  1               5                  10                  15

Ala Leu His Ile Met Asn Asp Leu Leu Lys Ala Gly Tyr Thr Val Ile
             20                  25                  30

Gly Ser Gly Arg Ser Gln Glu Lys Asn Asp Gly Leu Leu Lys Lys Phe
         35                  40                  45

Asn Asn Asn Pro Lys Leu Ser Met Glu Ile Val Glu Asp Ile Ala Ala
     50                  55                  60

Pro Asn Ala Phe Asp Glu Val Phe Lys Lys His Gly Lys Glu Ile Lys
```

-continued

```
65                  70                  75                  80

Ile Val Leu His Thr Ala Ser Pro Phe His Phe Glu Thr Thr Asn Phe
                85                  90                  95

Glu Lys Asp Leu Leu Thr Pro Ala Val Asn Gly Thr Lys Ser Ile Leu
            100                 105                 110

Glu Ala Ile Lys Lys Tyr Ala Ala Asp Thr Val Glu Lys Val Ile Val
        115                 120                 125

Thr Ser Ser Thr Ala Ala Leu Val Thr Pro Thr Asp Met Asn Lys Gly
    130                 135                 140

Asp Leu Val Ile Thr Glu Glu Ser Trp Asn Lys Asp Thr Trp Asp Ser
145                 150                 155                 160

Cys Gln Ala Asn Ala Val Ala Ala Tyr Cys Gly Ser Lys Lys Phe Ala
                165                 170                 175

Glu Lys Thr Ala Trp Glu Phe Leu Lys Glu Asn Lys Ser Ser Val Lys
            180                 185                 190

Phe Thr Leu Ser Thr Ile Asn Pro Gly Phe Val Phe Gly Pro Gln Met
        195                 200                 205

Phe Ala Asp Ser Leu Lys His Gly Ile Asn Thr Ser Ser Gly Ile Val
    210                 215                 220

Ser Glu Leu Ile His Ser Lys Val Gly Gly Glu Phe Tyr Asn Tyr Cys
225                 230                 235                 240

Gly Pro Phe Ile Asp Val Arg Asp Val Ser Lys Ala His Leu Val Ala
                245                 250                 255

Ile Glu Lys Pro Glu Cys Thr Gly Gln Arg Leu Val Leu Ser Glu Gly
            260                 265                 270

Leu Phe Cys Cys Gln Glu Ile Val Asp Ile Leu Asn Glu Glu Phe Pro
        275                 280                 285

Gln Leu Lys Gly Lys Ile Ala Thr Gly Glu Pro Ala Thr Gly Pro Ser
    290                 295                 300

Phe Leu Glu Lys Asn Ser Cys Lys Phe Asp Asn Ser Lys Thr Lys Lys
305                 310                 315                 320

Leu Leu Gly Phe Gln Phe Tyr Asn Leu Lys Asp Cys Ile Val Asp Thr
                325                 330                 335

Ala Ala Gln Met Leu Glu Val Gln Asn Glu Ala
            340                 345
```

<210> SEQ ID NO 12
<211> LENGTH: 1041
<212> TYPE: RNA
<213> ORGANISM: s. cerevisiae

<400> SEQUENCE: 12

```
augacuacug auaccacugu uuucguuucu ggcgcaaccg guuucauugc ucuacacauu      60

augaacgauc uguugaaagc uggcuauaca gucaucggcu cagguagauc ucaagaaaaa     120

aaugauggcu ugcucaaaaa auuuaauaac aaucccaaac uaucgaugga aauuguggaa     180

gauauugcug cuccaaacgc cuuugaugaa guuuucaaaa aacaugguaa ggaaauuaag     240

auugugcuac acacugccuc cccauuccau uuugaaacua ccaauuuuga aaaggauuua     300

cuaaccccug cagugaacgg uacaaaaucu aucuuggaag cgauuaaaaa auaugcugca     360

gacacuguug aaaaaguuau uguuacuucg ucuacugcug cucuggugac accuacagac     420

augaacaaag gagauuuggu gaucacggag gagaguugga auaaggauac augggacagu     480

ugucaagcca acgccguugc cgcauauugu ggcucgaaaa aguuugcuga aaaaacugcu     540
```

-continued

```
ugggaauuuc uuaaagaaaa caagucuagu gucaaauuca cacuauccac uaucaauccg    600

ggauucguuu uugguccuca aauguuugca gauucgcuaa aacauggcau aaauaccucc    660

ucagggaucg uaucugaguu aauucauucc aagguaggug gagaauuuua uaauuacugu    720

ggcccauuua uugacgugcg ugacguuucu aaagcccacc uaguugcaau ugaaaaacca    780

gaauguaccg gccaaagauu aguauugagu gaagguuuau ucugcuguca agaaaucguu    840

gacaucuuga acgaggaauu cccucaauua aagggcaaga uagcuacagg ugaaccugcg    900

accgguccaa gcuuuuuaga aaaaaacucu ugcaaguuug acaauucuaa gacaaaaaaa    960

cuacugggau uccaguuuua caauuuaaag gauugcauag uugacaccgc ggcgcaaaug   1020

uuagaaguuc aaaaugaagc c                                             1041
```

```
<210> SEQ ID NO 13
<211> LENGTH: 1044
<212> TYPE: DNA
<213> ORGANISM: s. cerevisiae
<220> FEATURE:
<221> NAME/KEY: CDS
<222> LOCATION: (1)..(1044)

<400> SEQUENCE: 13

atg act act gaa aaa acc gtt gtt ttt gtt tct ggt gct act ggt ttc      48
Met Thr Thr Glu Lys Thr Val Val Phe Val Ser Gly Ala Thr Gly Phe
  1               5                  10                  15

att gct cta cac gta gtg gac gat tta tta aaa act ggt tac aag gtc      96
Ile Ala Leu His Val Val Asp Asp Leu Leu Lys Thr Gly Tyr Lys Val
             20                  25                  30

atc ggt tcg ggt agg tcc caa gaa aag aat gat gga ttg ctg aaa aaa     144
Ile Gly Ser Gly Arg Ser Gln Glu Lys Asn Asp Gly Leu Leu Lys Lys
         35                  40                  45

ttt aag agc aat ccc aac ctt tca atg gag att gtc gaa gac att gct     192
Phe Lys Ser Asn Pro Asn Leu Ser Met Glu Ile Val Glu Asp Ile Ala
     50                  55                  60

gct cca aac gct ttt gac aaa gtt ttt caa aag cac ggc aaa gag atc     240
Ala Pro Asn Ala Phe Asp Lys Val Phe Gln Lys His Gly Lys Glu Ile
 65                  70                  75                  80

aag gtt gtc ttg cac ata gct tct ccg gtt cac ttc aac acc act gat     288
Lys Val Val Leu His Ile Ala Ser Pro Val His Phe Asn Thr Thr Asp
                 85                  90                  95

ttc gaa aag gat ctg cta att cct gct gtg aat ggt acc aag tcc att     336
Phe Glu Lys Asp Leu Leu Ile Pro Ala Val Asn Gly Thr Lys Ser Ile
            100                 105                 110

cta gaa gca atc aaa aat tat gcc gca gac aca gtc gaa aaa gtc gtt     384
Leu Glu Ala Ile Lys Asn Tyr Ala Ala Asp Thr Val Glu Lys Val Val
        115                 120                 125

att act tct tct gtt gct gcc ctt gca tct ccc gga gat atg aag gac     432
Ile Thr Ser Ser Val Ala Ala Leu Ala Ser Pro Gly Asp Met Lys Asp
    130                 135                 140

act agt ttc gtt gtc aat gag gaa agt tgg aac aaa gat act tgg gaa     480
Thr Ser Phe Val Val Asn Glu Glu Ser Trp Asn Lys Asp Thr Trp Glu
145                 150                 155                 160

agt tgt caa gct aac gcg gtt tcc gca tac tgt ggt tcc aag aaa ttt     528
Ser Cys Gln Ala Asn Ala Val Ser Ala Tyr Cys Gly Ser Lys Lys Phe
                165                 170                 175

gct gaa aaa act gct tgg gat ttt ctc gag gaa aac caa tca agc atc     576
Ala Glu Lys Thr Ala Trp Asp Phe Leu Glu Glu Asn Gln Ser Ser Ile
            180                 185                 190

aaa ttt acg cta tca acc atc aac cca gga ttt gtt ttt ggc cct cag     624
Lys Phe Thr Leu Ser Thr Ile Asn Pro Gly Phe Val Phe Gly Pro Gln
```

-continued

```
        195                200                205

cta ttt gcc gac tct ctt aga aat gga ata aat agc tct tca gcc att      672
Leu Phe Ala Asp Ser Leu Arg Asn Gly Ile Asn Ser Ser Ser Ala Ile
    210                215                220

att gcc aat ttg gtt agt tat aaa tta ggc gac aat ttt tat aat tac      720
Ile Ala Asn Leu Val Ser Tyr Lys Leu Gly Asp Asn Phe Tyr Asn Tyr
225                230                235                240

agt ggt cct ttt att gac gtt cgc gat gtt tca aaa gct cat tta ctt      768
Ser Gly Pro Phe Ile Asp Val Arg Asp Val Ser Lys Ala His Leu Leu
                245                250                255

gca ttt gag aaa ccc gaa tgc gct ggc caa aga cta ttc tta tgt gaa      816
Ala Phe Glu Lys Pro Glu Cys Ala Gly Gln Arg Leu Phe Leu Cys Glu
            260                265                270

gat atg ttt tgc tct caa gaa gcg ctg gat atc ttg aat gag gaa ttt      864
Asp Met Phe Cys Ser Gln Glu Ala Leu Asp Ile Leu Asn Glu Glu Phe
        275                280                285

cca cag tta aaa ggc aag ata gca act ggc gaa cct ggt agc ggc tca      912
Pro Gln Leu Lys Gly Lys Ile Ala Thr Gly Glu Pro Gly Ser Gly Ser
    290                295                300

acc ttt ttg aca aaa aac tgc tgc aag tgc gac aac cgc aaa acc aaa      960
Thr Phe Leu Thr Lys Asn Cys Cys Lys Cys Asp Asn Arg Lys Thr Lys
305                310                315                320

aat tta tta gga ttc caa ttt aat aag ttc aga gat tgc att gtc gat     1008
Asn Leu Leu Gly Phe Gln Phe Asn Lys Phe Arg Asp Cys Ile Val Asp
                325                330                335

act gcc tcg caa tta cta gaa gtt caa agt aaa agc                     1044
Thr Ala Ser Gln Leu Leu Glu Val Gln Ser Lys Ser
            340                345


<210> SEQ ID NO 14
<211> LENGTH: 348
<212> TYPE: PRT
<213> ORGANISM: s. cerevisiae

<400> SEQUENCE: 14

Met Thr Thr Glu Lys Thr Val Val Phe Val Ser Gly Ala Thr Gly Phe
  1               5                  10                  15

Ile Ala Leu His Val Val Asp Asp Leu Leu Lys Thr Gly Tyr Lys Val
            20                  25                  30

Ile Gly Ser Gly Arg Ser Gln Glu Lys Asn Asp Gly Leu Leu Lys Lys
        35                  40                  45

Phe Lys Ser Asn Pro Asn Leu Ser Met Glu Ile Val Glu Asp Ile Ala
     50                  55                  60

Ala Pro Asn Ala Phe Asp Lys Val Phe Gln Lys His Gly Lys Glu Ile
 65                  70                  75                  80

Lys Val Val Leu His Ile Ala Ser Pro Val His Phe Asn Thr Thr Asp
                85                  90                  95

Phe Glu Lys Asp Leu Leu Ile Pro Ala Val Asn Gly Thr Lys Ser Ile
            100                 105                 110

Leu Glu Ala Ile Lys Asn Tyr Ala Ala Asp Thr Val Glu Lys Val Val
        115                 120                 125

Ile Thr Ser Ser Val Ala Ala Leu Ala Ser Pro Gly Asp Met Lys Asp
    130                 135                 140

Thr Ser Phe Val Val Asn Glu Glu Ser Trp Asn Lys Asp Thr Trp Glu
145                 150                 155                 160

Ser Cys Gln Ala Asn Ala Val Ser Ala Tyr Cys Gly Ser Lys Lys Phe
                165                 170                 175
```

-continued

```
Ala Glu Lys Thr Ala Trp Asp Phe Leu Glu Glu Asn Gln Ser Ser Ile
            180                 185                 190

Lys Phe Thr Leu Ser Thr Ile Asn Pro Gly Phe Val Phe Gly Pro Gln
        195                 200                 205

Leu Phe Ala Asp Ser Leu Arg Asn Gly Ile Asn Ser Ser Ser Ala Ile
    210                 215                 220

Ile Ala Asn Leu Val Ser Tyr Lys Leu Gly Asp Asn Phe Tyr Asn Tyr
225                 230                 235                 240

Ser Gly Pro Phe Ile Asp Val Arg Asp Val Ser Lys Ala His Leu Leu
                245                 250                 255

Ala Phe Glu Lys Pro Glu Cys Ala Gly Gln Arg Leu Phe Leu Cys Glu
            260                 265                 270

Asp Met Phe Cys Ser Gln Glu Ala Leu Asp Ile Leu Asn Glu Glu Phe
        275                 280                 285

Pro Gln Leu Lys Gly Lys Ile Ala Thr Gly Glu Pro Gly Ser Gly Ser
    290                 295                 300

Thr Phe Leu Thr Lys Asn Cys Cys Lys Cys Asp Asn Arg Lys Thr Lys
305                 310                 315                 320

Asn Leu Leu Gly Phe Gln Phe Asn Lys Phe Arg Asp Cys Ile Val Asp
                325                 330                 335

Thr Ala Ser Gln Leu Leu Glu Val Gln Ser Lys Ser
            340                 345
```

<210> SEQ ID NO 15
<211> LENGTH: 1044
<212> TYPE: RNA
<213> ORGANISM: s. cerevisiae

<400> SEQUENCE: 15

```
augacuacug aaaaaaccgu uguuuuuguu ucuggugcua cugguuucau ugcucuacac     60

guaguggacg auuuauuaaa aacugguuac aaggucaucg guucggguag gucccaagaa    120

aagaaugaug gauugcugaa aaaauuuaag agcaauccca accuuucaau ggagauuguc    180

gaagacauug cugcuccaaa cgcuuuugac aaaguuuuuc aaaagcacgg caaagagauc    240

aagguugucu ugcacauagc uucuccgguu cacuucaaca ccacugauuu cgaaaaggau    300

cugcuaauuc cugcugugaa ugguaccaag uccauucuag aagcaaucaa aaauuaugcc    360

gcagacacag ucgaaaaagu cguuauuacu ucuucuguug cugcccuugc aucucccgga    420

gauaugaagg acacuaguuu cguugucaau gaggaaaguu ggaacaaaga uacuugggaa    480

aguugucaag cuaacgcggu uuccgcauac ugugguucca agaaauuugc ugaaaaaacu    540

gcuugggauu uucucgagga aaaccaauca agcaucaaau uuacgcuauc aaccaucaac    600

ccaggauuug uuuuuggccc ucagcuauuu gccgacucuc uuagaaaugg aauaaauagc    660

ucuucagcca uuauugccaa uuugguuagu uauaaauuag gcgacaauuu uuauaauuac    720

aguggucuu uuauugacgu ucgcgauguu ucaaaagcuc auuuacuugc auuugagaaa    780

cccgaaugcg cuggccaaag acuauucuua ugugaagaua uguuuugcuc ucaagaagcg    840

cuggauaucu ugaaugagga auuuccacag uuaaaaggca agauagcaac uggcgaaccu    900

gguagcggcu caaccuuuuu gacaaaaaac ugcugcaagu gcgacaaccg caaaaccaaa    960

aauuuauuag gauuccaauu uaauaaguuc agagauugca uugucgauac ugccucgcaa   1020

uuacuagaag uucaaaguaa aagc                                           1044
```

<210> SEQ ID NO 16

```
<211> LENGTH: 1270
<212> TYPE: DNA
<213> ORGANISM: z. rouxii
<220> FEATURE:
<223> OTHER INFORMATION: T at position 574 is T, A  or C; T at position
      733 is T or C; T at position 862 is T or C; A at position 1008 is
      A or G;
<223> OTHER INFORMATION: A at position 382 is A or T; A at position 740
      is A or G; A at position 910 is A or G;
<223> OTHER INFORMATION: T at position 469 is T or C; T at position 871
      is T or C; T at position 1036 is T or C;
<223> OTHER INFORMATION: A at position 307 is A or T; T at position 649
      is T or C; T at position 913 is T or C;
<223> OTHER INFORMATION: A at position 889 is A or G; T at position 1138
      is T or C;
<223> OTHER INFORMATION: T at position 868 is T or C; T at position 838
      is T or C; T at position 1004 is T or C; A at
      position 1008 is A or G;
<223> OTHER INFORMATION: A at position 896 is A or G; T at position 974
      is T or C; T at position 1024 is T or G.

<400> SEQUENCE: 16

tgaatggtta ttttagcaat tgctgtgtga ggcactgacc taaagatgtg tataaatagt     60

gggactgtgt actcatgagg atcaatacat gtataaactt accatacttt cacacaagtc    120

aacttagaat caatcaatca atcaattaat caagctatac aatatgacaa aagtcttcgt    180

aacaggtgcc aacggattcg ttgctcaaca cgtcgttcat caactattag aaaagaacta    240

tacagtggtt ggatctgtcc gttcaactga gaaaggtgat aaattagcta aattgctaaa    300

caatccaaaa ttttcatatg agattattaa agatatggtc aattcgagag atgaattcga    360

taaggcttta caaaaacatt cagatgttga aattgtctta catactgctt caccagtctt    420

cccaggtggt attaaagatg ttgaaaaaga aatgatccaa ccagctgtta atggtactag    480

aaatgtcttg ttatcaatca aggataactt accaaatgtc aagagatttg tttacacttc    540

ttcattagct gctgtccgta ctgaaggtgc tggttatagt gcagacgaag ttgtcaccga    600

agattcttgg aacaatattg cattgaaaga tgccaccaag gatgaaggta cagcttatga    660

ggcttccaag acatatggtg aaaaagaagt ttggaatttc ttcgaaaaaa ctaaaaatgt    720

taatttcgat tttgccatca tcaacccagt ttatgtcttt ggtcctcaat tatttgaaga    780

atacgttact gataaattga acttttccag tgaaatcatt aatagtataa taaaaggtga    840

aaagaaggaa attgaaggtt atgaaattga tgttagagat attgcaagag ctcatatctc    900

tgctgttgaa aatccagcaa ctacacgtca aagattaatt ccagcagttg caccatacaa    960

tcaacaaact atcttggatg ttttgaatga aaacttccca gaattgaaag gtaaaatcga   1020

tgttgggaaa ccaggttctc aaaatgaatt tattaaaaaa tattataaat tagataactc   1080

aaagaccaaa aaagttttag gttttgaatt catttcccaa gagcaaacaa tcaaagatgc   1140

tgctgctcaa atcttgtccg ttaaaaatgg aaaaaaataa gtgaactaga cctgtcacta   1200

tcagattatt agagttctgt atagattaaa gtgtgaaaat gtattagaat cataatttta   1260

taatatgcct                                                          1270


<210> SEQ ID NO 17
<211> LENGTH: 338
<212> TYPE: PRT
<213> ORGANISM: z. rouxii
<220> FEATURE:
<223> OTHER INFORMATION: Xaa at position 282 is Lys or Arg; Xaa at
      position 193 is Ile or Val; Xaa at position 250 is Asn or Lys;
      Xaa at position 245 is Ile or Val.

<400> SEQUENCE: 17
```

-continued

```
Met Thr Lys Val Phe Val Thr Gly Ala Asn Gly Phe Val Ala Gln His
  1               5                  10                  15

Val Val His Gln Leu Leu Glu Lys Asn Tyr Thr Val Val Gly Ser Val
             20                  25                  30

Arg Ser Thr Glu Lys Gly Asp Lys Leu Ala Lys Leu Leu Asn Asn Pro
         35                  40                  45

Lys Phe Ser Tyr Glu Ile Ile Lys Asp Met Val Asn Ser Arg Asp Glu
     50                  55                  60

Phe Asp Lys Ala Leu Gln Lys His Ser Asp Val Glu Ile Val Leu His
 65                  70                  75                  80

Thr Ala Ser Pro Val Phe Pro Gly Gly Ile Lys Asp Val Glu Lys Glu
                 85                  90                  95

Met Ile Gln Pro Ala Val Asn Gly Thr Arg Asn Val Leu Leu Ser Ile
            100                 105                 110

Lys Asp Asn Leu Pro Asn Val Lys Arg Phe Val Tyr Thr Ser Ser Leu
        115                 120                 125

Ala Ala Val Arg Thr Glu Gly Ala Gly Tyr Ser Ala Asp Glu Val Val
    130                 135                 140

Thr Glu Asp Ser Trp Asn Asn Ile Ala Leu Lys Asp Ala Thr Lys Asp
145                 150                 155                 160

Glu Gly Thr Ala Tyr Glu Ala Ser Lys Thr Tyr Gly Glu Lys Glu Val
                165                 170                 175

Trp Asn Phe Phe Glu Lys Thr Lys Asn Val Asn Phe Asp Phe Ala Ile
            180                 185                 190

Xaa Asn Pro Val Tyr Val Phe Gly Pro Gln Leu Phe Glu Glu Tyr Val
        195                 200                 205

Thr Asp Lys Leu Asn Phe Ser Ser Glu Ile Ile Asn Ser Ile Ile Lys
    210                 215                 220

Gly Glu Lys Lys Glu Ile Glu Gly Tyr Glu Ile Asp Val Arg Asp Ile
225                 230                 235                 240

Ala Arg Ala His Xaa Ser Ala Val Glu Xaa Pro Ala Thr Thr Arg Gln
                245                 250                 255

Arg Leu Ile Pro Ala Val Ala Pro Tyr Asn Gln Gln Thr Ile Leu Asp
            260                 265                 270

Val Leu Asn Glu Asn Phe Pro Glu Leu Xaa Gly Lys Ile Asp Val Gly
        275                 280                 285

Lys Pro Gly Ser Gln Asn Glu Phe Ile Lys Lys Tyr Tyr Lys Leu Asp
    290                 295                 300

Asn Ser Lys Thr Lys Lys Val Leu Gly Phe Glu Phe Ile Ser Gln Glu
305                 310                 315                 320

Gln Thr Ile Lys Asp Ala Ala Ala Gln Ile Leu Ser Val Lys Asn Gly
                325                 330                 335

Lys Lys
```

KETOREDUCTASE GENE AND PROTEIN FROM YEAST

CROSS-REFERENCE

This application is a continuation-in-part of allowed U.S. patent application Ser. No. 09/182,985, filed Oct. 30, 1998 (incorporated herein by reference) which claims the benefit of U.S. Provisional Application No. 60/064,195, filed Nov. 4, 1997.

FIELD OF INVENTION

This invention relates to recombinant DNA technology. In particular the invention pertains to the generation and use of recombinant hosts harboring genetic mutations which provide for increased expression levels of a fungal ketoreductase polypeptide useful in bioenzymatic processes for the stereospecific reduction of ketones.

BACKGROUND OF THE INVENTION 2,3 Benzodiazepine derivatives are potent antagonists of the AMPA (α-amino-3-hydroxy-5 methylisoxazole-4-propionic acid) class of receptors in the mammalian central nervous system (See I. Tarnawa et al. In *Amino Acids: Chemistry, Biology and Medicine*, Eds. Lubec and Rosenthal, Leiden, 1990). These derivative compounds have potentially widespread applications as neuroprotective agents, particularly as anti-convulsants. One series of 2,3 benzodiazepines is considered particularly advantageous for such use, and this series of compounds has the following general formula:

(I)

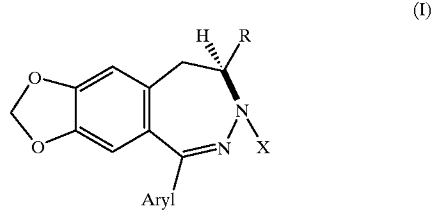

Wherein R is hydrogen or $C_1$–$C_{10}$ alkyl; and

X is hydrogen, $C_1$–$C_{10}$ alkyl, acyl, aryl, amido or carboxyl, or a substituted derivative thereof.

The clinical potential for these compounds has led to interest in developing more efficient synthetic methods. Biologically-based methods in which a ketoreductase enzyme provides a stereospecific reduction in a whole-cell process using fungal cells have been described in U.S. patent application Ser. No. 08/413,036. U.S. patent application Ser. No. 09/182,985 described the cloning of a ketoreductase gene from *Z.rouxii*, recombinant host cells that express the ketoreductase gene, and methods for stereospecifically reducing a ketone using either the recombinantly expressed ketoreductase or host cells expressing the cloned ketoreductase.

Maximizing expression levels of commercially important recombinantly expressed proteins is a common objective in the realm of biotechnology. Traditionally, protein properties have been modified by engineering changes in the DNA, mRNA, or polypeptide sequence based on a structural and/or functional understanding of that particular molecule, and testing for an improvement in the property which is being optimized. However, attempts to rationally alter one property of a recombinantly expressed polypeptide are often tedious, information intensive efforts. Additionally, these pursuits of a optimally expressed polypeptide often result in alterations which improve a targeted property at the expense of other important previously existing characteristics.

Recently, molecular "breeding" and directed evolution techniques have gained favor as methods of optimizing a particular protein's characteristics (Ness et al., (1999), DNA shuffling of subgenomic sequences of subtilisin, *Nat. Biotechnol.,* 17 (9):893). Directed evolution procedures are typically used to make desired changes in the characteristics of a protein absent specific knowledge of the genetic sequence or protein structure which confers that characteristic to the molecule. Changes in enzyme specific activity, substrate specificity, thermal stability, chemical stability, and other properties have been successfully modified by this approach (see Ness, et al.). The procedure typically involves incorporating random mutations into a genetic sequence, and/or inducing random recombination between similar coding nucleotide sequences, and screening or selecting for altered but desirable phenotypes in hosts expressing the resulting mutations.

Subsequent to the selection of hosts exhibiting the desired or improved upon properties, sequence analysis often reveals that the mutated coding sequences contain a combination of missense and silent mutations. Backcrossing against the unmated wild type sequence is generally employed to remove mutations that do not contribute to the desired property of the protein and could potentially have detrimental effects on untargeted but desired properties of the original molecule. In at least one relevant example the expression level of an enzyme increased measurably as a result of mutations in the promoter region of a targeted gene (Stemmer et al., (1994), Rapid evolution of a protein in vitro by DNA shuffling, Nature 370:389–391). Back-crossing resulted in a protein having the same property as the best mutant after all four silent mutations had been reverted back to the wild type sequence. Likewise, Ness et. al. (J. E. Ness, et al., DNA shuffling of subgenomic sequences of subtilisin, Nature Biotechnology 17: 893–896, 1999) reported directed evolution experiments resulted in hosts having altered expression levels. Ness et al. suggested that this phenotype was likely attributable to recombination within the coding sequence which affected secretion or maturation of the expressed protein product.

The present invention provides a method of increasing the ability of a recombinant host cell to express an hetereologous polypeptide which is more efficient, and less labor and knowledge intensive than current methods. The present invention also provides for mutated ketoreductase encoding polynucleotides which are expressed in recombinant host cells at much greater levels than the wild-type polynucleotides.

BRIEF SUMMARY OF THE INVENTION

The present invention relates to increased expression of polypeptides. The present invention is based on the discovery that silent mutations within the coding region of a polynucleotide can have unexpected and profound effects upon the expression level of the polypeptide encoded thereby. Ketoreductase encoding polynucleotide sequences are disclosed which exhibit increased levels of expression of ketoreductase.

Accordingly, the present invention relates to an isolated DNA molecule encoding a ketoreductase enzyme from *Z. rouxii*, said DNA molecule comprising a nucleotide sequence identified as SEQ ID NO:1.

In particularly preferred embodiments the invention is directed to isolated DNA molecules encoding a ketoreductase protein, wherein said DNA molecules comprise any one of the polynucleotide sequences identified in SEQ ID NO:16.

Having the cloned ketoreductase encoding nucleic acid molecules enables the production of recombinant ketoreductase proteins, and the production of recombinant host cells expressing said proteins, wherein said recombinant cells can be used in a stereospecific reduction of ketones.

The invention also provides the protein products of said nucleic acids, in substantially purified form. Also provided are methods for the formation of chiral alcohols using a purified ketoreductase enzyme, or recombinant host cells that express said nucleic acid molecules.

In another embodiment the present invention relates to a substantially purified ketoreductase protein molecule from *Z. rouxii*.

In another embodiment the present invention relates to a ketoreductase protein molecule from *Z. rouxii*, wherein said protein molecule comprises the sequence identified as SEQ ID NO:2.

In particularly preferred embodiments the invention is directed to a ketoreductase protein molecule wherein said protein molecule comprises any one of the sequences identified in SEQ ID NO:17.

In a further embodiment the present invention relates to a ribonucleic acid molecule encoding ketoreductase protein, said ribonucleic acid molecule comprising the sequence identified as SEQ ID NO:3.

In particularly preferred embodiments the invention is directed to a ribonucleic acid molecule encoding ketoreductase protein, said ribonucleic acid molecule arising from the transcription of any one of the polynucleotide sequences identified in SEQ ID NO:16.

In yet another embodiment, the present invention relates to a recombinant DNA vector that incorporates a ketoreductase encoding polynucleotide of the present invention in operable-linkage to gene expression sequences, enabling said polynucleotide to be transcribed and translated in a host cell.

In still another embodiment the present invention relates to host cells that have been transformed or transfected with a recombinant DNA vector of the present invention such that said ketoreductase gene is expressed in the host cell.

In a still further embodiment, the present invention relates to a method for producing chiral alcohols using recombinant host cells that express an exogenously introduced ketoreductase gene of the present invention.

In yet another embodiment, the present invention relates to a method for producing chiral alcohols using recombinant host cells that have been transformed or transfected with a ketoreductase gene of the present invention derived from *Z. rouxii*, or *S. cerevisiae*.

In yet another embodiment, the present invention relates to a method for producing chiral alcohols using a purified fungal ketoreductase.

DETAILED DESCRIPTION OF THE INVENTION

Definitions

SEQ ID NO:1–SEQ ID NO:3 comprises the DNA, protein, and RNA sequences of ketoreductase from *Z. rouxii*.

SEQ ID NO:4–SEQ ID NO:6 comprises the DNA, protein, and RNA sequences of gene YDR541c from *S. cerevisiae*.

SEQ ID NO:7–SEQ ID NO:9 comprises the DNA, protein, and RNA sequences of YOL151w from *S. cerevisiae*.

SEQ ID NO:10–SEQ ID NO:12 comprises the DNA, protein, and RNA sequences of YGL157w from *S. cerevisiae*.

SEQ ID NO:13–SEQ ID NO:15 comprises the DNA, protein, and RNA sequences of YGL039w from *S. cerevisiae*.

SEQ ID NO:16–SEQ ID NO:17 comprises DNA and protein sequences, respectively, generated by directed evolution experiments targeting wild-type *Z. rouxii* ketoreductase which result in ketoreductase encoding polynucleotides which are expressed at higher levels than wild-type polynucleotides as identified in SEQ ID NO:1.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" or "expression vector" as used herein refers to any recombinant DNA cloning vector, for example a plasmid or phage, in which a promoter and other regulatory elements are present thereby enabling transcription of an inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil. As used herein "complementary" means that at least one of two hybridizing strands is fully base-paired with the other member of said hybridizing strands, and there are no mismatches. Moreover, at each nucleotide position of said one strand, an "A" is paired with a "T", a "T" is paired with an "A", a "G" is paired with a "C", and a "C" is paired with a "G".

The term "conservative" in reference to an amino acid change or substitution is intended to indicate an amino acid has been replaced with a similar amino acid. Similar amino acids are amino acids that, because of size, charge, polarity and conformation, are more readily substituted without significantly affecting the structure and/or function of the protein. Thus, one skilled in the art generally does not expect a "conservative" amino acid change or substitution to result in any measurable difference in any particular characteristic, property, and/or activity of a polypeptide having a particular conservative amino acid substitution. Specific examples of amino acid changes or substitutions considered to be conservative are known in the art. These examples include, but are not limited to, the non-polar amino acids Glycine, Alanine, Valine, Isoleucine, and Leucine; the non-polar aromatic amino acids Phenylalanine, Tryptophan, and Tyrosine; the neutral polar amino acids Serine, Threonine, Cysteine, Glutamine, Asparagine, and Methionine; the negatively charged amino acids Lysine, Arginine, and Histidine; the positively charged amino acids Aspartate and Glutamate, represent groups of conservative amino acids. Substitution of any one for another in the same group would generally be considered to be a "conservative" substitution by one skilled in the art (See generally, James D. Watson et al., *Molecular Biology of the Gene* (1987)).

"Host cell" refers to any eucaryotic, procaryotic, or fusion or other cell or pseudo cell or membrane-containing construct that is suitable for propagating and/or expressing an isolated nucleic acid that is introduced into a host cell by any suitable means known in the art (e.g., but not limited to, transformation or transfection, or the like), or induced to express an endogenous nucleic acid encoding a polypeptide according to the present invention. The cell can be part of a tissue or organism, isolated in culture or in any other suitable form.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA. An inducible promoter is one that is regulatable by environmental signals, such as carbon source, heat, metal ions, chemical inducers, etc.; a constitutive promoter generally is expressed at a constant level and is not regulatable.

A "probe" as used herein is a labeled nucleic acid compound which can hybridize wih another nucleic acid compound.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The terms "silent mutation" and "silent substitution" are used interchangeably throughout the present specification and are intended to denote a change in the nucleotide sequence of a polypeptide encoding polynucleotide which does not result in a change in the amino acid sequence of the polypeptide encoded thereby.

"Substantially identical" means a sequence having sufficient homology to hybridize under stringent conditions and/or be at least 90% identical to a sequence disclosed herein.

The term "stringency" relates to nucleic acid hybridization conditions. High stringency conditions disfavor non-homologous base pairing. Low stringency conditions have the opposite effect. Stringency may be altered, for example, by changes in temperature, denaturants, and salt concentration. Typical high stringency conditions comprise hybridizing at 50° C. to 65° C. in 5× SSPE and 50% formamide, and washing at 50° C. to 65° C. in 0.5× SSPE; typical low stringency conditions comprise hybridizing at 35° C. to 37° in 5× SSPE and 40% to 45% formamide and washing at 42° C. in 1×–2× SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of $NaH_2PO_4 \cdot H_2O$, and 7.4 g of EDTA in 800 ml of $H_2O$. The pH is adjusted with NaOH and the volume brought to 1 liter.

"SSC" denotes a hybridization and wash solution comprising sodium chloride and sodium citrate at pH 7. A 20× solution of SSC is made by dissolving 175 g of NaCl and 88 g of sodium citrate in 800 ml of $H_2O$. The volume is brought to 1 liter after adjusting the pH with 10 N NaOH.

The term "transformed" refers to any process for altering the DNA content of a host cell. This includes in vitro transformation procedures such as calcium phosphate or DEAE-dextran-mediated transfection, electroporation, nuclear injection, phage infection, or such other means for effecting controlled DNA uptake as are known in the art.

The ketoreductase gene encodes a novel enzyme that catalyzes an asymmetric reduction of selected ketone substrates (See Equation 1 and Table 1). The ketoreductase enzymes disclosed herein are members of the carbonyl reductase enzyme class. Carbonyl reductases are involved in the reduction of xenobiotic carbonyl compounds (Hara et. al, *Arch. Biochem. Biophys.,* 244, 238–247, 1986) and have been classified into the short-chain dehydrogenase/reductase (SDR) enzyme superfamily (Jörnvall et. al, *Biochemistry,* 34, 6003–6013, 1995) and the single-domain reductase-epimerase-dehydrogenase (RED) enzyme superfamily (Labesse et. al, *Biochem. J.,* 304, 95–99, 1994).

The ketoreductases of this invention are able to effectively reduce a variety of α-ketolactones, α-ketolactams, and diketones (Table 1).

Equation 1

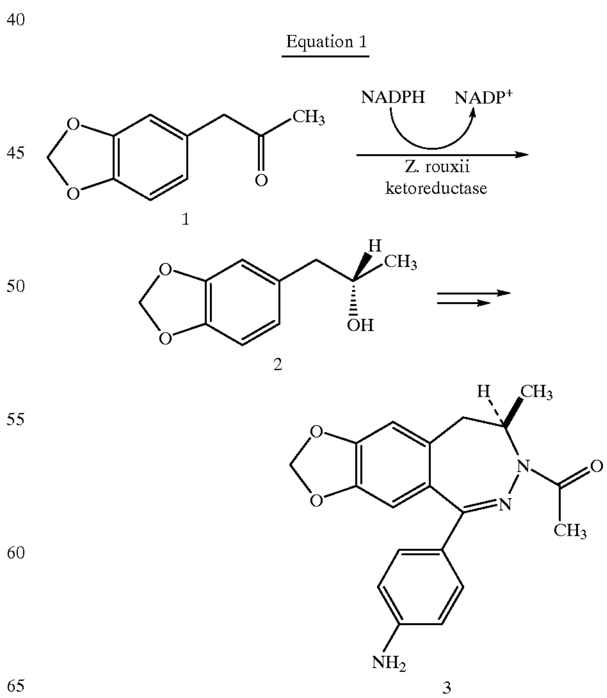

TABLE 1

| Substrate specificity of wild-type ketoreductase from *Z. rouxii* (SEQ ID NO: 2). | | |
|---|---|---|
| Compound | Concentration (mM) | % Relative Activity |
| 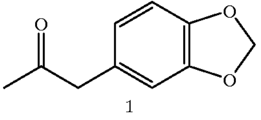 1 | 3 | 100 |
| 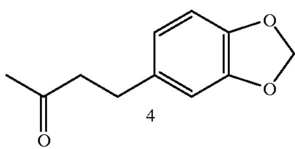 4 | 5 | 18 |
| 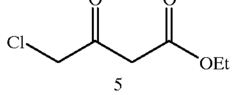 5 | 5 | 42 |
| 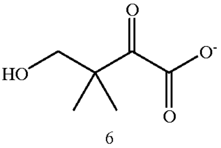 6 | 4 | 37 |
| 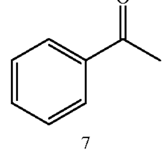 7 | 0.6 | 4 |
| 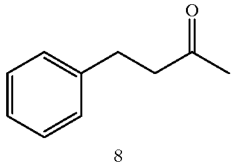 8 | 0.6 | 0 |
| 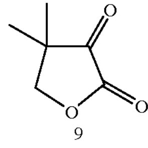 9 | 3 | 194 |
| 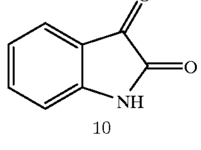 10 | 0.8 | 86 |

TABLE 1-continued

| Substrate specificity of wild-type ketoreductase from *Z. rouxii* (SEQ ID NO: 2). | | |
|---|---|---|
| Compound | Concentration (mM) | % Relative Activity |
| 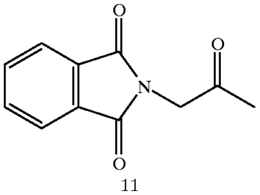 11 | 0.6 | 17 |
| 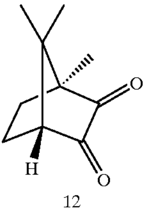 12 | 5 | 100 |
| 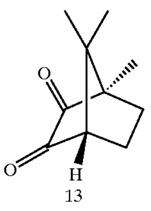 13 | 5 | 32 |

The ketoreductase gene of *Z. rouxii* comprises a DNA sequence designated herein as SEQ ID NO:1. Those skilled in the art will recognize that owing to the degeneracy of the genetic code (i.e. 64 codons which encode 20 amino acids), numerous “silent” substitutions or “silent” mutations of nucleotide base pairs could be introduced into the sequence identified as SEQ ID NO:1 without altering the identity of the encoded amino acid(s) or protein product as shown in SEQ ID NO:2. Although “silent” substitutions or “silent” mutations of a given polynucleotide sequence are “silent” as far as the identity of the encoded amino acid or protein product is concerned, such substitutions or mutations can confer advantageous attributes to hosts expressing the altered sequences. Preferred “silent” mutations of the present invention are those which result in increased expression, volumetric potency, enzymatic activity, and/or production levels as compared to an unaltered polynucleotide upon expression in a particular host. Polynucleotides incorporating at least one “silent” mutation which results in increased expression, volumetric potency, enzymatic activity, and/or production levels of a particular polypeptide are intended to be within the scope of this invention. Preferred mutant ketoreductase polynucleotides include variants of the polynucleotide as shown in SEQ ID NO:1 which result in increased expression, volumetric potency, enzymatic activity, and/or production levels of the encoded ketoreductase enzyme. Most preferred mutant *Z. rouxii* ketoreductase polynucleotides include variants of the polynucleotide as shown in SEQ ID NO:1 which result in increased expression, volumetric potency, enzymatic activity, and/or production levels of the encoded ketoreductase enzyme wherein the polynucleotide of SEQ ID NO: 1 further comprises at least one silent mutation selected from the group consisting of 307T, 382T, 469C, 574C, 574A, 649C, 733C, 838A, 862C, 868C, 871C, 889G, 910G, 974C, 1004C, 1024G, 1036C, and 1138C.

It is also known in the art that "silent" mutations may result in the creation of codons which are known in the art to be preferred by a host harboring and expressing said polynucleotides. Targeted mutagenesis directed towards incorporating specific "silent" mutations which create codons, selected from among alternative codons specifying the same amino acid, on the basis of preferential expression in the host microorganism (e.g., *E. Coli*) projected to be transformed is a well-known means of increasing expression levels of a targeted polypeptide (see U.S. Pat. No. 5,082,767 which is incorporated herein by reference). Furthermore, targeted "silent" mutations are often incorporated into a polynucleotide in order to relieve known secondary structures which are thought to impede translational processes for the purpose of increasing expression levels of a targeted polypeptide. Similarly, targeted "silent" mutations are often incorporated into a polynucleotide in order to decrease the susceptibility of the encoded mRNA to degradation which subsequently may lead to improved expression levels of the encoded polypeptide.

The untargeted, randomly generated "silent" mutations disclosed herein do not result in codons known to be preferred in *E. coli* nor would one skilled in the art expect them to result in altered secondary structure which would influence expression levels. Therefore, another embodiment of the present invention includes a method for effecting increased expression levels of a heterologous polypeptide, as well as any functional fragments thereof, in a recombinant host which comprises the generation of "silent" mutations within a polynucleotide encoding a polypeptide wherein the said mutations are not directed towards incorporating codons known to be preferred by a particular host nor altering secondary structures to increase mRNA stability and/or expression levels.

Gene Isolation Procedures

Those skilled in the art will recognize that the ketoreductase gene may be obtained by a plurality of applicable recombinant DNA techniques including, for example, polymerase chain reaction (PCR) amplification, hybridization to a genomic or cDNA library, or de novo DNA synthesis.(See e.g., J. Sambrook et al. *Molecular Cloning,* 2d Ed. Chap. 14 (1989)).

Methods for constructing cDNA libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the ketoreductase gene or fragment thereof could be isolated by PCR amplification from a human cDNA library prepared from a tissue in which said gene is expressed, using oligonucleotide primers targeted to any suitable region of SEQ ID NO:1. Methods for PCR amplification are widely known in the art. See e.g. *PCR Protocols: A Guide to Method and Application*, Ed. M. Innis et.al., Academic Press (1990). The amplification reaction comprises template DNA, suitable enzymes, primers, nucleoside triphosphates, and buffers, and is conveniently carried out in a DNA Thermal Cycler (Perkin Elmer Cetus, Norwalk, Conn.). A positive result is determined by detecting an appropriately-sized DNA fragment following gel electrophoresis.

Protein Production Methods

One embodiment of the present invention relates to the substantially purified ketoreductase enzyme (identified herein as SEQ ID NO:2) encoded by the *Z. rouxii* ketoreductase gene (identified herein as SEQ ID NO:1).

Skilled artisans will recognize that the proteins of the present invention can be synthesized by a number of different methods, such as chemical methods well known in the art, including solid phase peptide synthesis or recombinant methods. Both methods are described in U.S. Pat. No. 4,617,149, incorporated herein by reference. The proteins of the invention can also be purified by well known methods from a culture of cells that produce the protein, for example, *Z. rouxii.*

The principles of solid phase chemical synthesis of polypeptides are well known in the art and may be found in general texts in the area. See, e.g., H. Dugas and C. Penney, *Bioorganic Chemistry* (1981) Springer-Verlag, N.Y., 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems.

The protein of the present invention can also be produced by recombinant DNA methods using a cloned ketoreductase gene. Recombinant methods are preferred if a high yield is desired. Expression of the cloned gene can be carried out in a variety of suitable host cells, well known to those skilled in the art. For this purpose, the ketoreductase gene is introduced into a host cell by any suitable means, well known to those skilled in the art. While chromosomal integration of the cloned gene is within the scope of the present invention, it is preferred that the gene be cloned into a suitable extra-chromosomally maintained expression vector so that the coding region of the ketoreductase gene is operably-linked to a constitutive or inducible promoter.

The basic steps in the recombinant production of the ketoreductase protein are:

a) constructing a natural, synthetic or semi-synthetic DNA encoding a ketoreductase protein;

b) integrating said DNA into an expression vector in a manner suitable for expressing the ketoreductase protein, either alone or as a fusion protein; or integrating said DNA into a host chromosome such that said DNA expresses ketoreductase;

c) transforming or otherwise introducing said vector into an appropriate eucaryotic or prokaryotic host cell forming a recombinant host cell, d) culturing said recombinant host cell in a manner to express the ketoreductase protein; and e) recovering and substantially purifying the ketoreductase protein by any suitable means, well known to those skilled in the art.

The wild-type ketoreductase protein of *Z. rouxii* comprises a polypeptide designated herein as SEQ ID NO:1. Those skilled in the art will recognize that amino acid substitutions can be incorporated into the polypeptides of the present invention without altering the enzymatic activity of the molecule. Using well known theories, one skilled in the art can reasonably predict protein variants which are likely retain biological activity and those which are not. Specifically, conserved amino acid substitutions can be readily incorporated into the polypeptides of the present invention with the expectation that result expression levels, volumetric potency, enzymatic activity, and/or production levels will not be affected. Polynucleotides which incorporate at least one conservative amino acid substitution and which result in increased expression, volumetric potency, enzymatic activity, and/or production levels of the encoded polypeptide upon expression in a host are intended to be within the scope of this invention. Preferred ketoreductase polypeptides include variants of the polypeptide as shown in SEQ ID NO:2 wherein said variants comprise at least one conservative amino acid subsitutions as compared to the polypeptide shown in SEQ ID NO:2. More preferred ketoreductase polypeptide variants include any one of the polypeptides as identified in SEQ ID NO:17. Most preferred ketoreductase polypeptide variants include those encoded by any one of the polynucleotides as identified in SEQ ID NO:16.

Expressing Recombinant Ketoreductase Protein in Procaryotic and Eucaryotic Host Cells Procaryotes may be employed in the production of the ketoreductase protein. For example, the *Escherichia coli* K12 strain 294 (ATCC No. 31446) or strain RV308 is particularly useful for the prokaryotic expression of foreign proteins. Other strains of *E. coli*, bacilli such as *Bacillus subtilis*, enterobacteriaceae such as *Salmonella typhimuriuin* or *Serratia marcescans*, various Pseudomonas species and other bacteria, such as Streptomyces, may also be employed as host cells in the cloning and expression of the recombinant proteins of this invention.

Promoter sequences suitable for driving the expression of genes in procaryotes include beta-lactamase [e.g. vector pGX2907, ATCC 39344, contains a replicon and beta-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein(s) of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to procaryotes, a variety of eucaryotic microorganisms including yeast are suitable host cells. The yeast *Saccharomyces cerevisiae* is the most commonly used eucaryotic microorganism. Other yeasts such as *Kluyveromyces lactis, Schizosaccharomyces pombe*, and *Pichia pastoris* are also suitable. For expression in Saccharomyces, the plasmid YRp7 (ATCC-40053), for example, may be used. See, e.g., L. Stinchcomb, et al., *Nature,* 282:39 (1979); J. Kingsman et al., *Gene,* 7:141 (1979); S. Tschemper et. al., *Gene,* 10:157 (1980). Plasmid YRp7 contains the TRP1 gene which provides a selectable marker for use in a trp1 auxotrophic mutant.

Purification of Recombinantly-Produced Ketoreductase Protein

An expression vector carrying a cloned ketoreductase gene is transformed or transfected into a suitable host cell using standard methods. Host cells may comprise procaryotes, such as *E. coli*, or simple eucaryotes, such as *Z. rouxii, S. cerevisiae, S. pombe, P. pastoris*, and *K. Lactis*. Cells which contain the vector are propagated under conditions suitable for expression of an encoded ketoreductase protein. If the recombinant gene has been placed under the control of an inducible promoter then suitable growth conditions would incorporate the appropriate inducer. The recombinantly-produced protein may be purified from cellular extracts of transformed cells by any suitable means.

In a preferred process for protein purification, the ketoreductase gene is modified at the 5' end to incorporate several histidine residues at the amino terminus of the ketoreductase protein product. This "histidine tag" enables a single-step protein purification method referred to as "immobilized metal ion affinity chromatography" (IMAC), essentially as described in U.S. Pat. No. 4,569,794 which hereby is incorporated by reference. The IMAC method enables rapid isolation of substantially pure ketoreductase protein starting from a crude cellular extract.

Other embodiments of the present invention comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one codon. Because these alternative nucleic acid sequences would encode the same amino acid sequences, the present invention further comprises these alternate nucleic acid sequences.

The ketoreductase genes disclosed herein, for example SEQ ID NO:1, may be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). A DNA segment corresponding to a ketoreductase gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

In an alternative methodology, namely PCR, a DNA sequence comprising a portion or all of SEQ ID NO:1, SEQ ID NO:4, SEQ ID NO:7, SEQ ID NO:10, or SEQ ID NO:13 can be generated from a suitable DNA source, for example *Z. rouxii* or *S. cerevisiae* genomic DNA or cDNA. For this purpose, suitable oligonucleotide primers targeting any of the polynucleotides identified in SEQ ID NO:1, SEQ ID NO:4, SEQ ID NO:7, SEQ ID NO:10, SEQ ID NO:13, SEQ ID NO: 16, or any region therein are prepared, as described in U.S. Pat. No. 4,889,818, which hereby is incorporated by reference. Protocols for performing the PCR are disclosed in, for example, *PCR Protocols: A Guide to Method and Applications*, Ed. Michael A. Innis et al., Academic Press, Inc. (1990).

Procedures for generating random mutations in a targeted DNA or cDNA molecule are known to one skilled in the art. These procedures may include, but are not limited to, techniques such as those described hereinafter which rely on PCR performed under conditions favorable for mutagenesis of the resulting polynucleotide product.

The ribonucleic acids of the present invention may be prepared using the polynucleotide synthetic methods discussed supra, or they may be prepared enzymatically using RNA polymerase to transcribe a ketoreductase DNA template. See e.g., J. Sambrook, et. al., supra, at 18.82–18.84.

This invention also provides nucleic acids, RNA or DNA, which are complementary to SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, or any of the polynucleotides identified in SEQ ID NO:16.

The present invention also provides probes and primers useful for a variety of molecular biology techniques including, for example, hybridization screens of genomic, subgenomic, or cDNA libraries. A nucleic acid compound comprising SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, any of the polynucleotides identified in SEQ ID NO:16, any complementary sequence thereof, or a fragment thereof, which is at least 18 base pairs in length, and which will selectively hybridize to DNA encoding a ketoreductase, is provided. Preferably, the 18 or more base pair compound is DNA. See e.g. B. Wallace and G. Miyada, "Oligonucleotide Probes for the Screening of Recombinant DNA Libraries," In *Methods in Enzymology*, Vol. 152, 432–442, Academic Press (1987).

Probes and primers can be prepared by enzymatic methods well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. The preferred nucleic acid vectors are those which comprise DNA. The most preferred recombinant DNA vectors comprise a isolated DNA sequence selected from the group consisting of SEQ ID NO:1, SEQ ID NO:4, SEQ ID NO:7, SEQ ID NO:10, SEQ ID NO:13, and any of the polynucleotides as shown in SEQ ID NO:16.

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably-linked gene. Constitutive promoters are further suitable in instances for which secretion or extra-cellular export is desireable. The skilled artisan will recognize a number of inducible promoters which respond to a variety of inducers, for example, carbon source, metal ions, and heat. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing the extra-cellular export of a resulting polypeptide.

Host cells harboring the nucleic acids disclosed herein are also provided by the present invention. Suitable host cells include procaryotes, such as *E. coli*, or simple eucaryotes, such as fungal cells, which have been transfected or transformed with a vector which comprises a nucleic acid of the present invention.

The present invention also provides a method for constructing a recombinant host cell capable of expressing SEQ ID NO:2, SEQ ID NO:5, SEQ ID NO:8, SEQ ID NO:11, SEQ ID NO:14, or any of the polypeptides as shown in SEQ ID NO:17 said method comprising transforming or otherwise introducing into a host cell a recombinant DNA vector that comprises an isolated DNA sequence which encodes SEQ ID NO:2, SEQ ID NO:5, SEQ ID NO:8, SEQ ID NO:11, SEQ ID NO:14, or any of the polynucleotides as shown in SEQ ID NO:16. Preferred vectors for expression are those which comprise SEQ ID NO:1 or any of the polynucleotides as shown in SEQ ID NO:16. Transformed host cells may be cultured under conditions well known to skilled artisans such that SEQ ID NO:2, SEQ ID NO:5, SEQ ID NO:8, SEQ ID NO:11, SEQ ID NO:14, or any one of the polypeptides as shown in SEQ ID NO:17 is expressed, thereby producing a ketoreductase protein in the recombinant host cell.

For the purpose of identifying or developing inhibitors or other modifiers of the enzymes disclosed herein, or for identifying suitable substrates for bioconversion, it would be desirable to identify compounds that bind and/or inhibit, or otherwise modify, the ketoreductase enzyme and its associated activity. A method for determining agents that will modify the ketoreductase activity comprises contacting the ketoreductase protein with a test compound and monitoring the alteration of enzyme activity by any suitable means.

The instant invention provides such a screening system useful for discovering compounds which bind the ketoreductase protein, said screening system comprising the steps of:

a) preparing ketoreductase protein;

b) exposing said ketoreductase protein to a test compound;

c) quantifying a modulation of activity by said compound.

Utilization of the screening system described above provides a means to determine compounds which may alter the activity of ketoreductase. This screening method may be adapted to automated procedures such as a PANDEX® (Baxter-Dade Diagnostics) system, allowing for efficient high-volume screening of potential modifying agents.

In such a screening protocol, ketoreductase is prepared as described herein, preferably using recombinant DNA technology. A test compound is introduced into a reaction vessel containing ketoreductase, followed by addition of enzyme substrate. For convenience the reaction can be coupled to the oxidation of NADPH, thereby enabling progress to be monitored spectrophotometrically by measuring the absorbance at 340 nm. Alternatively, substrate may be added simultaneously with a test compound. In one method radioactively or chemically-labeled compound may be used. The products of the enzymatic reaction are assayed for the chemical label or radioactivity by any suitable means. The absence or diminution of the chemical label or radioactivity indicates the degree to which the reaction is inhibited.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing a Ketoreductase Gene in a Homologous or Heterologous Host A plasmid comprising the *Z. rouxii* ketoreductase gene suitable for expressing said gene in a host cell, for example *E. coli* (DE3) strains, contains an origin of replication (Ori), an antibiotic resistance gene (i.e., Tet or Amp), useful for selecting cells which have incorporated the vector following a tranformation procedure, and further comprises the lacI gene for repression of the lac operon, as well as the T7 promoter and T7 terminator sequences in operable linkage to the coding region of the ketoreductase gene. Parent plasmid pET11A (obtained from Novogen, Madison, Wis.) was linearized by digestion with endonucleases NdeI and BamHI. Linearized pET11A was ligated to a DNA fragment bearing NdeI and BamHI sticky ends and further comprising the coding region of the *Z. rouxii* ketoreductase gene.

The ketoreductase gene is isolated most conveniently by the PCR. Genomic DNA from *Z. rouxii* isolated by standard methods was used for amplification of the ketoreductase gene. Primers are synthesized corresponding to the 5' and 3' ends of the gene (SEQ ID NO:1) to enable amplification of the coding region.

The ketoreductase gene (nucleotides 164 through 1177 of SEQ ID NO:1) ligated into the vector may be modified at the 5' end (amino terminus of encoded protein) in order to simplify purification of the encoded ketoreductase protein. For this purpose, an oligonucleotide encoding 8 histidine residues and a factor Xa cleavage site can be inserted after the ATG start codon at nucleotide positions 164 to 166 of SEQ ID NO:1. Placement of the histidine residues at the amino terminus of the encoded protein does not affect its activity and serves only to enable the IMAC one-step protein purification procedure.

For expression analysis in *E. coli*, recombinant plasmid DNA containing the complete *Z. rouxii* cDNA was digested with Nde I-Bam HI to release a 1.0-kb fragment. This fragment was then directly cloned into an expression vector (PHMM 176 (rop-)) downstream of the T7 promoter to produce pHRP2 that was transformed into *E. coli* -DE3-lysogen based expression cells for protein production. Transformed RQ228 host cells were grown overnight at 37° C. in LB medium containing tetracycline (12.5 μg/mL), diluted, and induced at an $OD_{600}$ of 0.6–0.8 in 50-mL LB medium plus 100 μM IPTG for 2–4 hrs. Extraction of ketoreductase enzyme from bacteria was performed using 3-mL B-PER reagent (Pierce, Rockland, Ill.) per bacterial pellet. The lysate was cleared by centrifugation at 15,000 rpm for 15 min.

EXAMPLE 2

Purification of Ketoreductase from *Z. rouxii*

Approximately 1 gram of *Z. rouxii* cell paste was resuspended in Lysing Buffer, comprising 50 mM Tris-Cl pH 7.5, 2 mM EDTA supplemented with pepstatin (1 μg/mL), leupeptin (1.25 μg/mL), aprotinin (2.5 μg/mL), and AEBSF (25 μg/mL). The cells were lysed using a DynoMill (GlenMills, Inc. Clifton, N.J.) equipped with 0.5–0.75 mm lead free beads under continuous flow conditions according to the manufacturer's recommended use. After four complete passes through the DynoMill, the material was centrifuged twice (25,000×g for 30 minutes at 4° C.). Solid ammonium sulfate (291 g/liter) was added slowly to the resulting clarified cell extract with stirring at 4° C. to achieve 50% saturation. After 1 hour, the mixture was centrifuged at 23,000×g for 30 minutes. The supernatant was then brought to 85% saturation by the addition of solid ammonium sulfate (159 g/liter) and stirred for 1 h at 4° C. before centrifugation (23,000×g for 30 min). The resultant 50–85% ammonium sulfate pellet was resuspended in 600 mL of Lysing Buffer and the residual ammonium sulfate was removed by dialysis against the same buffer at 4° C. The desalted material was centrifuged twice to remove particulate matter (23,000×g for 30 min) and 700–800 Units of the clarified material was loaded onto a Red-120 dye affinity column (32 mm×140 mm) equilibrated in 50 mM Tris-Cl pH 7.5, 1 mM $MgCl_2$, pepstatin (1 μg/mL), leupeptin (1.25 μg/mL), and aprotinin (2.5 μg/mL). Reductase activity was eluted from the column at a flowrate of 8 mL/min under the following conditions: 1) a 10 minute linear gradient from 0–0.3 M NaCl; 2) 13 minutes at 0.3 M NaCl; 3) a 60 minute linear gradient from 0.3–1.5 M NaCl. The fractions containing reductase activity were pooled, and changed to 20 mM potassium phosphate buffer (pH 7.2), pepstatin (1 μg/mL), leupeptin (1.25 μg/mL), and aprotinin (2.5 μg/mL) by dialysis at 4° C. The sample was clarified by centrifugation (23,000×g for 30 min) and 400 Units was loaded onto a Bio-Scale CHT-I hydroxyapatite column (15 mm×113 mm, Bio-Rad, Inc.) equilibrated in the same buffer that had been made 5% in glycerol. Reductase activity was eluted from the column at a flowrate of 5.0 mL/min in a sodium chloride step gradient consisting of 5 minutes at 0 M NaCl, a gradient step to 0.7 M NaCl which was maintained for 10 minutes, and then a 20 minute linear gradient from 0.7–1.0 M NaCl. The fractions containing reductase activity were pooled and desalted with 20 mM potassium phosphate buffer (pH 7.2), pepstatin A (1 μg/mL), leupeptin (1.25 μug/mL), and aprotinin (2.5 μg/mL) by dialysis at 4° C. The sample (100–200 Units) was loaded onto a Bio-Scale CHT-I hydroxyapatite column (10 mm×64 mm) equilibrated in the same buffer which had been made 5% in glycerol. Reductase activity was eluted from the column at a flowrate of 2.0 mL/min in a 25 minute linear gradient from 0 to 50% 400 mM potassium phosphate (pH 6.8), 5% glycerol. Fractions containing reductase activity were pooled and changed into 10 mM Tris-Cl (pH 8.5) by dialysis at 4° C. The sample was then made 10% in glycerol, concentrated to 0.4 mg/mL by ultrafiltration (Amicon, YM-10), and stored at −70° C.

EXAMPLE 3

Reductase Activity Using the Ketoreductase from *Z. rouxii*

Reductase activity was measured using a suitable substrate and a partially purified or substantially purified ketoreductase from *Z. rouxii*. Activity was measured as a function of the absorbance change at 340 nm, resulting from the oxidation of NADPH. The 1 ml assay contained a mixture of 3.0 mM 3,4-methylenedioxyphenyl acetone, 162 μM NADPH, 50 mM MOPS buffer (pH 6.8), and 0.6 mU of ketoreductase and was carried out at 26° C. Reaction mixtures were first equilibrated at 26° C. for 10 min in the absence of NADPH, and then initiated by addition of NADPH. The absorbance was measured at 340 nm every 15 seconds over a 5 minute period; the change in absorbance was found to be linear over that time period. The kinetic parameters for 3,4-methylenedioxyphenyl acetone were determined at an NADPH concentration of 112 $\mu$M and a 3,4-methylenedioxyphenyl acetone concentration that varied from 1.7 mM –7.2 mM. The kinetic parameters for NADPH were determined by maintaining the 3,4-methylenedioxyphenyl acetone concentration at 3 mM and the NADPH concentration was varied from 20.5 $\mu$M–236.0 $\mu$M. An extinction coefficient of 6220 $M^{-1}$ $cm^{-1}$ for NADPH absorbance at 340 nm was used to calculate the specific activity of the enzyme. For assays using isatin, the change in absorbance with time was measured at 414 nm using an extinction coefficient of 849 $M^{-1}$ $cm^{-1}$ to calculate activity. One Unit of activity corresponds to 1 $\mu$mol of NADPH consumed per minute. For assays carried out at differing pH values, 10 mM Bis-Tris and 10 mM Tris were adjusted to the appropriate pH with HCl. Kinetic parameters were determined by non-linear regression using the JMP® statistics and graphics program.

The ketoreductase assay of recombinant *E. coli* expressed ketoreductase was performed as described above with only slight modifications. Specifically, 100 $\mu$l crude extracts of recombinant *E. coli* expressed ketoreductase in 1-mL volumes containing 3 mM of 1 and 50 mM MOPS (pH 6.8) were equilibrated at room temperature for 5 min. Reactions were then initiated by addition of 5 mg NADPH. Following a 1-hr incubation at 37° C., reaction mixtures were extracted against mobile phase before being analyzed by HPLC.

EXAMPLE 4

Whole Cell Method for Stereoselective Reduction of Ketone Using Recombinant Yeast Cell A vector for expressing the cloned *Z. rouxii* ketoreductase gene (SEQ ID NO:1) in a procaryotic or fungal cell, such as *S. cerevisiae*, is constructed as follows. A 1014 base pair fragment of *Z rouxii* genomic DNA or cDNA, carrying the ketoreductase gene, is amplified by PCR using primers targeted to the ends of the coding region specified in SEQ ID NO:1. It is desireable that the primers also incorporate suitable cloning sites for cloning of said 1014 base pair fragment into an expression vector. The appropriate fragment encoding ketoreductase is amplified and purified using standard methods, for cloning into an expression vector.

A suitable vector for expression in *E. coli* and *S. cerevisiae* is pYX213 (available from Novagen, Inc., 597 Science Drive, Madison, Wis. 53711; Code MBV-029-10), a 7.5 Kb plasmid that carries the following genetic markers: ori, 2$\mu$ circle, $Amp^R$, CEN, URA3, and the GAL promoter, for high level expression in yeast. Downstream of the GAL promoter, pYX213 carries a multiple cloning site (MCS), which will accommodate the ketoreductase gene amplified in the preceding step. A recombinant plasmid is created by digesting pYX213 and the amplified ketoreductase gene with a restriction enzyme, such as BamH1, and ligating the fragments together.

A recombinant fungal expression vector carrying the *Z. rouxii* ketoreductase gene is transformed into a suitable $Ura^-$ strain of *S. cerevisiae*, using well known methods. $Ura^+$ transformants are selected on minimal medium lacking uracil.

Expression of the recombinant ketoreductase gene may be induced if desired by growing transformants in minimal medium that contains 2% galactose as the sole carbon source.

To carry out a whole cell stereospecific reduction, 3,4-methylenedioxyphenyl acetone is added to a culture of transformants to a concentration of about 10 grams per liter of culture. The culture is incubated with shaking at room temperature for 24 hours, and the presence of the chiral alcohol analyzed by HPLC.

EXAMPLE 5

Mutagenesis of wild-type *Z. rouxii* ketoreductase encoding cDNA sequence to generate recombinant *E. Coli* transformants exhibiting greater *Z. rouxii* ketoreductase volumetric potency activity Primers RP001 and RP004 (having the nucleotide sequences ttaattaagcggccgccatatgacaaaagtcttcgtaacaggtgccaac and ttaattaagcggccgcggatcctattattttttccatttttaacggac, respectively) were used to amplify under mutagenic PCR conditions a 1060 bp DNA fragment. PCR was performed under the following conditions: 5 ng template (plasmid DNA containing the wild-type *Z. rouxii* ketoreductase gene sequence prepared from a dam-positive *E. Coli* strain (DH5α), 10 mM Tris-HCl (pH 8.3 at 25° C.), 50 mM KCl, 7 mM $MgCl_2$, 0.01% (w/v) gelatin, 0.15 mM $MnCl_2$, 0.2 mM each of dATP and dGTP, 1.0 mM each of dCTP and dTTP, 0.3 $\mu$m of each primer, and 5 U Taq DNA polymerase (Promega) in a 100 $\mu$l final reaction volume. Cycling protocol: 94° C. for 2', 13 cycles of 94° C. 1', 50° C. 1', 72° C. 1', followed by 72° C. for 2' and a 4° C. soak in a Perkin-Elmer 9600 Thermocycler (Perkin-Elmer, Foster City, Calif.). No template and no primer controls were included.

The StEP procedure was performed essentially as described by Zhao et al. (Zhao et al., Molecular evolution by staggered extension process (StEP) in vitro recombination. *Nature Biotechnol.* 16, 258–261 (1998)). Briefly, 5 $\mu$l of 1:10 diluted mutagenized template DNA, 10 mM Tris-HCl (pH 9.0 at 25° C.), 50 mM KCl, 1.5 mM MgCl2, 0.2 mM each dNTPs, 0.06 $\mu$M each of RP001 and RP004 primers, and 2.5 U Taq DNA polymerase (Promega) in a 50 $\mu$l final reaction volume. Cycling conditions: 94° C. for 2', 90 cycles of 94° C. 30", 55° C. 15", followed by a 4° C. soak using a Perkin-Elmer 9600 Thermocycler. No template and no primer controls were included. Reaction products were electrophoresied in a 0.8% agarose gel. A discrete band of the correct size (approximately 1 kb) was band isolated from a smear of DNA fragments. DNA was purified away from agarose using GeneClean II (Bio 101, Vista, Calif.) and digested with Dpn I. In order to amplify the full-length product, standard PCR was then performed. Reaction conditions included: 1 $\mu$l (100 ng/$\mu$l) Dpn I digested StEP DNA, 10 mM Tris-HCl (pH 8.3 at 25° C.), 50 mM KCl, 1.5 mM MgCl2, 10% DMSO or 10% glycerol (included sometimes to enhance PCR), 0.2 mM each dNTPs, 0.5 each of RP001 and RP004 primers, and 2.5 U Taq DNA polymerase (Perkin-Elmer) in a 100 $\mu$l final reaction volume. Cycling conditions: 94° C. 2', 30 cycles of 94° C. 30", 55° C. 30", 72° C. 1', followed by 72° C. for 2' and a 4° C. soak.

The PCR-amplified, reassembled product was purified using the QIAquick PCR purification kit (Qiagen, Chatsworth, Calif.), restriction-digested with Nde I and Bam HI, followed by gel electrophoresis in a 0.8% agarose gel. The DNA band of the correct size was isolated and purified using the QIAquick gel extraction kit (Qiagen). Purified digested DNA products were ligated with vector generated by Nde I-Bam HI digestion of the pHMM176 expression vector. The resultant gene library was amplified in *E. coli*

DH5α and transferred into *E. coli* (DE3) strain competent cells. 1056 clones were picked and each was grown in 100 μl L-broth medium supplemented with 12.5 μg/μl tetracycline in twelve 96-well plates. Following overnight growth, the 96-well plate library was replicated to provide a working library. Glycerol to 17.5% was added to both libraries and the libraries were stored at −70° C.

To identify ketoreductase variants, a 96-well plate-screening assay was developed based on a scale down of the UV assay described in Example 3. Briefly, the working library described previously was replicated into 12 96-well plates containing 1 ml L-broth medium supplemented with 12.5 μg/μl tetracycline. From each well of the IPTG-induced/B-PER extracted 96-well plate, 10 μl of cellular extract was transferred to the corresponding wells of two new plates (library screened in duplicate, 24 plates total). To each well of the new plate was then added 60 μl of 50 mM MOPS (pH 6.8) plus 60 μl of 10 mM 3,4-methylene dioxyphenyl acetone (3 mM final concentration). Following a 10-min incubation at room temperature, the reaction was initiated by adding 70 μl of 571 μM NADPH (final concentration 200 μM). Ketoreductase activity was monitored in a 96-well plate reader (SPECTRAmax® Plus, Molecular Devices) at $OD_{340}$ every 15 sec for 10 min. A Biomek® 2000 Workstation was utilized to add/mix reagents to the 96-well plates. Sixteen out of 1056 clones screened showed improved ketoreductase activity. Activity was confirmed by assaying these sixteen (10 replicas for each clone) for activity against the substrate 3,4-methylenedioxyphenyl acetone. Out of the sixteen, nine variants exhibited statistically significant higher potency than parental control. These variants exhibited 1.8 to 14.9-fold greater volumetric potency than the parental control (see Tables 2 and 3).

TABLE 2

| Mutation Profile | | |
|---|---|---|
| Mutation Frequency: | 0.28% | (46) |
| Mutation Bias: | | |
| Location: | | |
| A or T: | 76% | (35) |
| G or C | 24% | (11) |
| Transitions: | 70% | (32) |
| Transversions: | 30% | (14) |
| Mutation Types: | | |
| Silent: | 28.3% | (13) |
| Missense: | 67.4% | (31) |
| Nonsense: | 4.3% | (2) |
| Clones Screened: | 100% | (1056) |
| Variants = Control Activity | 11% | (113) |
| Variants > Control Activity | 3% | (30) |
| Variants < Control Activity | 86% | (913) |

TABLE 3

Effects of DNA and Amino Acid Substitutions on Volumetric Potency of Ketoreductase Expression

| Mutant | Nucleotide Position* | Mutation | Codon Position | Amino Acid Position** | Amino Acid Substitution | Fold improvement[1] | Stat. confidence[2] |
|---|---|---|---|---|---|---|---|
| 7E8 | 574 | T to C | 3 | 137 | silent | 14.9 | 99.96% |
| | 733 | T to C | 3 | 190 | silent | | |
| | 862 | T to C | 3 | 233 | silent | | |
| | 1008 | A to G | 2 | 282 | Lys to Arg | | |
| 4D4 | 382 | A to T | 3 | 73 | silent | 11.3 | 99.99 |
| | 740 | A to G | 1 | 193 | Ile to Val | | |
| | 910 | A to G | 3 | 249 | silent | | |
| 8C5 | 469 | T to C | 3 | 102 | silent | 8.3 | 99.6 |
| | 871 | T to C | 3 | 236 | silent | | |
| | 1036 | T to C | 3 | 291 | silent | | |
| 7E10 | 307 | A to T | 3 | 48 | silent | 8.0 | 99.95 |
| | 649 | T to C | 3 | 162 | silent | | |
| | 913 | T to C | 3 | 250 | Asn to Lys | | |
| 5H3 | 889 | A to G | 3 | 242 | silent | 6.2 | 99.74 |
| | 1138 | T to C | 3 | 325 | silent | | |
| 1C5 | 868 | T to C | 3 | 235 | silent | 5.7 | 99.67 |
| 8D12 | 574 | T to A | 3 | 137 | silent | 4.0 | 99.32 |
| | 838 | T to A | 3 | 225 | silent | | |
| 5C4 | 1004 | T to C | 1 | 281 | silent | 3.8 | 98.9 |
| | 1008 | A to G | 2 | 282 | Lys to Arg | | |
| 8F5 | 896 | A to G | 1 | 245 | Ile to Val | 1.8 | 97.69 |
| | 974 | T to C | 1 | 271 | silent | | |
| | 1024 | T to G | 3 | 287 | silent | | |

*in reference to SEQ ID NO: 1

**in reference to SEQ ID NO: 2

[1]ketoreductase activity as compared to control (host expressing SEQ ID NO: 1).

[2]statistical confidence that host carrying mutant sequence shows volumetric potency different from control (wild-type).

We claim:

1. An isolated nucleic acid compound encoding a ketoreductase protein, said protein comprising the amino acid sequence which is selected from the group consisting of:

a) SEQ ID NO:2; and b) SEQ ID NO:17.

2. An isolated nucleic acid compound selected from the group consisting of:

a) SEQ ID NO:1, b) SEQ ID NO:3, c) SEQ ID NO:16, and d) a polynucleotide sequence complementary to a), b), or c).

3. A vector comprising an isolated nuleic acid compound selected from the group consisting of:

a) SEQ ID NO:1; and b) SEQ ID NO:16.

4. The vector of claim 3 wherein said isolated nucleic acid compound is operably-linked to a promoter sequence.

5. A recombinant host cell comprising a host cell which has been transformed with a vector according to claim 4.

6. The recombinant host cell of claim 5 wherein said host cell is one selected from the group consisting of *S. cerevisiae, Z. rouxii, Pichia pastoris*, and *E. coli.*

* * * * *